(12) United States Patent
Lennig et al.

(10) Patent No.: US 7,994,168 B2
(45) Date of Patent: *Aug. 9, 2011

(54) HEXAHYDRO-PYRAZINO[1,2-A] PYRIMIDINE-4,7-DIONE DERIVATIVES SUBSTITUTED WITH AMINO ACIDS

(75) Inventors: Petra Lennig, Mainz (DE); Siegfried Stengelin, Eppstein (DE); Thomas Klabunde, Frankfurt (DE); Matthias Gossel, Hofheim (DE); Pavel Safar, Tucson, AZ (US); James Spoonamore, Tucson, AZ (US); Gregory Merriman, Phillipsburg, NJ (US); Joseph T Klein, Neshanic, NJ (US); Brian Whiteley, Lebanon, NJ (US); Carolina Lanter, Audubon, PA (US); Kenneth Bordeau, Kintnersville, PA (US); Zhaoxia Yang, Rosselle Park, NJ (US); Martin Smrcina, Tucson, AZ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 279 days.

This patent is subject to a terminal disclaimer.

(21) Appl. No.: 11/677,067

(22) Filed: Feb. 21, 2007

(65) Prior Publication Data
US 2007/0197539 A1 Aug. 23, 2007

Related U.S. Application Data

(63) Continuation of application No. PCT/EP2005/008873, filed on Aug. 16, 2005.

(30) Foreign Application Priority Data

Aug. 31, 2004 (DE) .......... 10 2004 042 441

(51) Int. Cl.
C07D 487/04 (2006.01)
A61K 31/4985 (2006.01)
A61P 3/04 (2006.01)

(52) U.S. Cl. ...................... 514/249; 544/279

(58) Field of Classification Search .......... 514/249; 544/230, 279, 281
See application file for complete search history.

(56) References Cited

U.S. PATENT DOCUMENTS

| | | | |
|---|---|---|---|
| 2005/0004131 A1* | 1/2005 | Flohr et al. | 514/249 |
| 2005/0085483 A1* | 4/2005 | Flohr et al. | 514/249 |

FOREIGN PATENT DOCUMENTS

| | | |
|---|---|---|
| WO | WO 01/00210 | 1/2001 |
| WO | WO 01/16135 | 3/2001 |
| WO | WO 2004/072077 | 8/2004 |

OTHER PUBLICATIONS

Jonsson, et al., Acta Physiologica 2006; vol. 187, Supp. 659, Scand. Physiolog. Soc.'s Ann. Mtg.*
Sutton, et al., Peptides 29 (2008) 104-111.*
Nargund, et al., J. Med. Chem, 2006, vol. 49, #14, 4035-4043.*
Wikipedia, Derivative, http://en.wikipedia.org/wiki/Derivative_(chemistry), downloaded Mar. 11, 2011.*
Wikipedia, Protecting group, http://en.wikipedia.org/wiki/Protection_group, downloaded Mar. 11, 2011.*
Wikipedia, Ester, http://en.wikipedia.org/wiki/Ester_group, downloaded Mar. 11, 2011.*
Wikipedia, Functional group, http://en.wikipedia.org/wiki/Functional_group, downloaded Mar. 11, 2011.*
Wikipedia, Residue (chemistry), http://en.wikipedia.org/wiki/Residue_(chemistry), downloaded Mar. 11, 2011.*
Wikipedia, C-Terminus, http://en.wikipedia.org/wiki/C-terminus, downloaded Mar. 11, 2011.*

* cited by examiner

*Primary Examiner* — James O Wilson
*Assistant Examiner* — Cecilia M Jaisle
(74) *Attorney, Agent, or Firm* — Scully, Scott, Murphy & Presser, P.C.

(57) ABSTRACT

The invention relates to substituted hexahydropyrazino[1,2-a]pyrimidine-4,7-dione derivatives substituted with amino acids, and to the physiologically tolerated salts thereof, processes for their preparation and their use as medicaments.

2 Claims, No Drawings

HEXAHYDRO-PYRAZINO[1,2-A] PYRIMIDINE-4,7-DIONE DERIVATIVES SUBSTITUTED WITH AMINO ACIDS

FIELD OF THE INVENTION

Hexahydropyrazino[1,2-a]pyrimidine-4,7-dione derivatives substituted with amino acids, processes for their preparation and their use as medicaments The invention relates to substituted hexahydropyrazino[1,2-a]pyrimidine-4,7-dione derivatives and to the physiologically tolerated salts thereof.

BACKGROUND OF THE INVENTION

The invention was based on the object of providing compounds which bring about a weight reduction in mammals and are suitable for the prevention and treatment of obesity.

SUMMARY OF THE INVENTION

The invention therefore relates to compounds of the formula I,

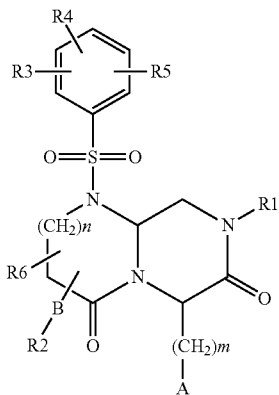

I in which the meanings are
A 3-12 membered mono-, bi- or spirobicyclic ring which may comprise one or more heteroatoms from the group of N, O and S and which 3-12 membered ring may have further substitutents such as F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;
R11, R12, R13, R14, R15 independently of one another H, $(C_1-C_6)$-alkyl, heterocycle;
n 0, 1;
m 0, 1, 2, 3, 4, 5, 6;
R1 R8, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkenylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9, $(C_1-C_4$-alkyl)-heterocycle, where the alkylene groups may be substituted one or more times by F;
R8, R9 independently of one another H, F, Cl, Br, I, OH, $CF_3$ aryl, heterocycle, $(C_3-C_8)$-cycloalkyl, where the rings or ring systems may be substituted up to 3 times by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl, $CONH_2$;
B a bond, —$(C_1-C_6)$-alkylene—$(C_2-C_6)$-alkenylene-, —$(SO_2)$—, —$(SO_2)$—$(C_1-C_6)$-alkylene-, —$(SO_2)$—$(C_2-C_6)$-alkenylene-, —(C=O)—, —(C=O)—$(C_1-C_6)$-alkylene-(C=O)—$(C_2-C_6)$-alkenylene-, —(C=O)NH—, —(C=O)—NH—$(C_1-C_6)$-alkylene-, —(C=O)—NH—$(C_2-C_6)$-alkenylene-, COO—, COO—$(C_1-C_6)$-alkylene-, COO—$(C_2-C_6)$-alkenylene-, —NH—$SO_2$—, —NH—$SO_2$—$(C_1-C_6)$-alkylene-, NH—$SO_2$—$(C_2-C_6)$-alkenylene-, —NR11-$SO_2$—, —NR11-$SO_2$—$(C_1-C_6)$-alkylene-, —NR11-$SO_2$—$(C_2-C_6)$-alkenylene-, —NH(CO)—, —NH(CO)—$(C_1-C_6)$-alkylene-, —NH(CO)—$(C_2-C_6)$-alkenylene-;
R2 a heterocycle, where the heterocycle is substituted by at least one amino acid or one amino acid derivative;
R3, R4, R5 independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl$(C_1-C_8)$-alkylene-aryl, O—$(C_1-C_8)$-alkylene-aryl, S-aryl, N($(C_1-C_6)$-alkyl$)_2$, $SO_2$—$CH_3$, COOH, COO—$(C_1-C_6)$-alkyl, CO—N($(C_1-C_6)$-alkyl$)_2$;
R6 H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, $(C_0-C_8)$-alkylene-aryl, O—$(C_0-C_8)$-alkylene-aryl, S-aryl, N($(C_1-C_6)$-alkyl$)_2$, $SO_2$—$CH_3$, COOH, COO—$(C_1-C_6)$-alkyl, CO—N($(C_1-C_6)$-alkyl$)_2$;
and the physiologically tolerated salts thereof.

DETAILED DESCRIPTION OF THE INVENTION

Preference is given to compounds of the formula I of the following structure Ia

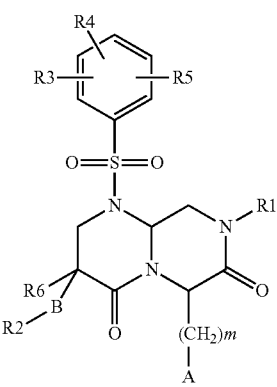

Ia in which the meanings are
A 3-12 membered mono-, bi- or spirobicyclic ring which may comprise one or more heteroatoms from the group of N, O and S and which 3-12 membered ring may have further substitutents such as F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO$(C_1-C_6)$-alkyl or COO—$(C_1-C_6)$-alkyl;

R11, R12, R13, R14, R15 independently of one another H, $(C_1-C_6)$-alkyl, heterocycle;

m 0, 1, 2, 3, 4, 5, 6;

R1 R8, $(C_1-C_6)$-alkyl, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9, $(C_1-C_4)$-alkyl-heterocycle, where the alkylene groups may be substituted one or more times by F;

R8, R9 independently of one another H, F, Cl, Br, I, OH, $CF_3$, aryl, heterocycle, $(C_3-C_8)$-cycloalkyl, where the rings or ring systems may be substituted up to 3 times by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl, $CONH_2$;

B a bond, —$(C_1-C_6)$-alkylene-, —$(C_2-C_6)$-alkenylene-, —$(SO_2)$—, —$(SO_2)$—$(C_1-C_6)$-alkylene-, —$(SO_2)$—$(C_2-C_6)$-alkenylene-, —(C=O)—, —(C=O)—$(C_1-C_6)$-alkylene-(C=O)—$(C_2-C_6)$-alkenylene-, —(C=O)NH—, —(C=O)—NH—$(C_1-C_6)$-alkylene-, —(C=O)—NH—$(C_2-C_6)$-alkenylene-, COO—, COO—$(C_1-C_6)$-alkylene-, COO—$(C_2-C_6)$-alkenylene-, —NH—$SO_2$—, —NH—$SO_2$—$(C_1-C_6)$-alkylene-, —NH—$SO_2$—$(C_2-C_6)$-alkenylene-, —NR11-$SO_2$—, —NR11-$SO_2$—$(C_1-C_6)$-alkylene-, —NR 11-$SO_2$—$(C_2-C_6)$-alkenylene-, —NH(CO)—, —NH(CO)—$(C_1-C_6)$-alkylene-, —NH(CO)—$(C_2-C_6)$-alkenylene-;

R2 a heterocycle, where the heterocycle is substituted by at least one amino acid or one amino acid derivative;

R3, R4, R5 independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl$(C_0-C_8)$-alkylene-aryl, O—$(C_0-C_8)$-alkylene-aryl, S-aryl, N(($C_1-C_6$)-alkyl)$_2$, $SO_2$—$CH_3$, COOH, COO—$(C_1-C_6)$-alkyl, CO—N(($C_1$-$C_6$)-alkyl)$_2$;

R6 H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, aryl, O-aryl, $(C_1-C_8)$-alkylene-aryl, O—$(C_1-C_8)$-alkylene-aryl, S-aryl, N(($C_1-C_6$)-alkyl)$_2$, $SO_2$—$CH_3$, COOH, COO—$(C_1-C_6)$-alkyl, CO—N(($C_1-C_6$)-alkyl)$_2$;

and the physiologically tolerated salts thereof.

Particular preference is given to compounds of the formula Ia
in which the meanings are A aryl, pyridyl, where the ring may have other substitutents such as F, Cl, Br, $NO_2$, $CF_3$, $OCF_3$, CN, $(C_1-C_6)$-alkyl, aryl, CON(R11)(R12), N(R13)(R14), OH, O—$(C_1-C_6)$-alkyl, S—$(C_1-C_6)$-alkyl, N(R15)CO($C_1-C_6$)-alkyl or COO—$(C_1-C_6)$-alkyl;

R11, R12, R13, R14, R15 independently of one another H, $(C_1-C_6)$-alkyl, heterocycle;

m 1;

R1 R8, $(C_1-C_6)$-alkyl, $(C_1-C_6)$-alkylene-R8, $(C_2-C_6)$-alkenylene-R9, $(SO_2)$—R8, $(SO_2)$—$(C_1-C_6)$-alkylene-R8, $(SO_2)$—$(C_2-C_6)$-alkenylene-R9, (C=O)—R8, (C=O)—$(C_1-C_6)$-alkylene-R8, (C=O)NH—R8, (C=O)—$(C_2-C_6)$-alkylene-R9, (C=O)—NH—$(C_1-C_6)$-alkylene-R8, (C=O)—NH—$(C_2-C_6)$-alkenylene-R9, COO—R8, COO—$(C_1-C_6)$-alkylene-R8, COO—$(C_2-C_6)$-alkenylene-R9, alkynylene-R9, $(C_1-C_4$-alkyl)-heterocycle, where alkylene may be substituted one or more times by F;

R8, R9 independently of one another H, F, Cl, Br, I, OH, $CF_3$, aryl, heterocycle, $(C_3-C_8)$-cycloalkyl, where the rings or ring systems may be substituted up to 3 times by F, Cl, Br, I, OH, $CF_3$, $NO_2$, CN, $OCF_3$, O—$(C_1-C_6)$-alkyl, $(C_1-C_6)$-alkyl, $NH_2$, CON(R11)(R12), N(R13)(R14), $SO_2$—$CH_3$, COOH, COO—$(C_1-C_6)$-alkyl, $CONH_2$;

B —NH(C=O)—;

R2 a nitrogen-containing heterocycle, where the heterocycle is substituted by at least one amino acid or one amino acid derivative;

R3 H

R4, R5 independently of one another H, F, Cl, Br, OH, $CF_3$, $OCF_3$, O—$(C_1-C_6)$-alkyl, $(C_1-C_6)$-alkyl;

R6 H;

and the physiologically tolerated salts thereof.

Very particular preference is given to compounds of the formula Ia
in which the meanings are A phenyl, pyridyl, where the ring may have other substitutents such as F, Cl, Br, $NO_2$, $CF_3$, $OCF_3$, CN, $(C_1-C_6)$-alkyl, aryl;

m 1;

R1 $(C_1-C_6)$-alkyl, $(C_3-C_8)$-cycloalkyl, where alkyl may be substituted one or more times by F;

B —NH(C=O)—;

R2 pyrrolidine, which is substituted by at least one amino acid or one amino acid derivative;

R3 H

R4 F, Cl, Br, OH, $CF_3$, $OCF_3$, O—$(C_1-C_6)$-alkyl, $(C_1-C_6)$-alkyl;

R5 F, Cl, Br, OH, $CF_3$, $OCF_3$, O—$(C_1-C_6)$-alkyl, $(C_1-C_6)$-alkyl;

R6 H;

and the physiologically tolerated salts thereof.

If radicals or substitutents may occur more than once in the compounds of the formula I, such as, for example, CON(R11)(R12), they may all have, independently of one another, the stated meanings and be identical or different.

The invention relates to compounds of the formula I in the form of their racemates, enantiomer-enriched mixtures and pure enantiomers, and to their diastereomers and mixtures thereof.

The alkyl, alkenyl and alkynyl radicals in the substituents A, R1, R2, R3, R4, R5, R6, R8, R9, R10, R11, R12, R13, R14, R15 may be either straight-chain, branched or optionally halogenated.

The term "aryl" means a phenyl or naphthyl group.

Heterocycle or heterocyclic radical means ring systems which, apart from carbon, also comprise heteroatoms such as, for example, nitrogen, oxygen or sulfur. This definition also includes ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyrazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

The corresponding N-oxides of these compounds are also included, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example, F, Cl, Br, I, $CF_3$, $NO_2$, $N_3$, CN, COOH, COO $(C_1-C_6)$alkyl, $CONH_2$, $CONH(C_1-C_6)$alkyl, $CON[(C_1-C_6)$alkyl$]_2$, $(C_1-C_6)$-alkyl, $(C_2-C_6)$-alkenyl, $(C_2-C_6)$-alkynyl, $O—(C_1-C_6)$-alkyl, where one or more than one, or all hydrogen(s) in the alkyl radicals may be replaced by fluorine; $PO_3H_2$, $SO_3H$, $SO_2—NH_2$, $SO_2NH(C_1-C_6)$-alkyl, $SO_2N[(C_1-C_6)$-alkyl$]_2$, $S—(C_1-C_6)$-alkyl, $S—(CH_2)_n$-phenyl, $SO—(C_1-C_6)$-alkyl, $SO—(CH_2)_n$-phenyl, $SO_2—(C_1-C_6)$-alkyl, $SO_2—(CH_2)_n$-phenyl, where n can be 0-6, and the phenyl radical may be substituted up to twice by F, Cl, Br, OH, $CF_3$, $NO_2$, CN, $OCF_3$, $O—(C_1-C_6)$-alkyl, $(C_1-C_6)$-alkyl, $NH_2$;
$C(NH)(NH_2)$, $NH_2$, $NH—(C_1-C_6)$-alkyl, $N((C_1-C_6)$-alkyl$)_2$, $NH(C_1-C_7)$-acyl, phenyl, $O—(CH_2)_n$-phenyl, where n may be 0-6, and where the phenyl ring may be substituted one to 3 times by F, Cl, Br, I, OH, $CF_3$, $NO_2$, CN, $OCF_3$, $O—(C_1-C_6)$-alkyl, $(C_1-C_6)$-alkyl, $NH_2$, $NH(C_1-C_6)$-alkyl, $N((C_1-C_6)$-alkyl$)_2$, $SO_2—CH_3$, COOH, COO—$(C_1-C_6)$-alkyl, $CONH_2$.

The term amino acids or amino acid residues means the stereoisomeric forms, i.e. D or L forms, of the following compounds:

| | | |
|---|---|---|
| alanine | glycine | proline |
| cysteine | histidine | glutamine |
| aspartic acid | isoleucine | arginine |
| glutamic acid | lysine | serine |
| phenylalanine | leucine | threonine |
| tryptophan | methionine | valine |
| tyrosine | asparagine | |

| | |
|---|---|
| 2-aminoadipic acid | 2-aminoisobutyric acid |
| 3-aminoadipic acid | 3-aminoisobutyric acid |
| beta-alanine | 2-aminopimelic acid |
| 2-aminobutyric acid | 2,4-diaminobutyric acid |
| 4-aminobutyric acid | desmosine |
| piperidic acid | 2,2-diaminopimelic acid |
| 6-aminocaproic acid | 2,3-diaminopropionic acid |
| 2-aminoheptanoic acid | N-ethylglycine |
| 2-(2-thienyl)-glycine | 3-(2-thienyl)-alanine |
| penicillamine | N-methylglycine |
| N-ethylasparagine | N-methylisoleucine |
| hydroxylysine | 6-N-methyllysine |
| allo-hydroxylysine | N-methylvaline |
| 3-hydroxyproline | norvaline |
| 4-hydroxyproline | norleucine |
| isodesmosine | ornithine |
| allo-isoleucine | 11-aminoundecanoic acid |

The amino acids have been abbreviated in accordance with the generally customary nomenclature (cf. Schröder, Lübke, The Peptides, Volume I, New York 1965, pages XXII-XXIII; Houben-Weyl, Methoden der Organischen Chemie [Methods of Organic Chemistry], Volume XV/1 and 2, Stuttgart 1974). The amino acid D-Asp is the D-form of aspartic acid. Peptides are acid amides from their chemical nature and are decomposed to amino acids on hydrolysis.

Amino acid derivatives mean protected amino acid, esters of amino acids, N-alkylated amino acids or α-alkylated amino acids.

The term amino acid-protective groups is to be understood as meaning suitable groups with which the functional groups of the side chains of the amino acid residues are protected (see, for example, T. W. Greene, P. G. M. Wuts, Protective Groups in Organic Synthesis, 2nd Edition, John Wiley and Sons, News York 1991). Those mainly used were: t-butyloxycarbonyl (BOC), 9-fluorenylmethoxy-carbonyl (Fmoc), benzyloxy-carbonyl (Z), 2-(3,5-dimethoxyphenyl)prop-2-yloxycarbonyl (Ddz), methyl, t-butyl, trityl and S-t-butyl.

Pharmaceutically acceptable salts are particularly suitable for medical applications because their solubility in water is higher than the initial or basic compounds. These salts must have a pharmaceutically acceptable anion or cation. Suitable pharmaceutically acceptable acid addition salts of the compounds of the invention are salts of inorganic acids such as hydrochloric acid, hydrobromic acid, phosphoric, metaphosphoric, nitric, sulfamic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. The chloride salt is particularly preferably used for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in nontherapeutic, for example in vitro, applications.

The term "physiologically functional derivative" used herein refers to any physiologically tolerated derivative of a compound according to the invention of the formula I, for example an ester, which is able on administration to a mammal such as, for example, a human to form (directly or indirectly) a compound of the formula I or an active metabolite thereof.

The physiologically functional derivatives also include prodrugs of the compounds according to the invention. Such prodrugs can be metabolized in vivo to a compound according to the invention. These prodrugs may themselves be active or not.

The compounds according to the invention may also exist in various polymorphous forms, for example as amorphous and crystalline polymorphous forms. All polymorphous forms of the compounds according to the invention lie within the scope of the invention and are a further aspect of the invention.

All references hereinafter to "compound(s) of formula (I)" refer to compound(s) of the formula (I) as described above, and the salts, solvates and physiologically functional derivatives thereof as described herein.

The amount of a compound of formula (I) which is necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1.0 to 1000 mg, typically from 10 to 600 mg. In the case of pharmaceutically acceptable salts, the aforementioned weight data are based on the weight of the salt—underlying free compound. For the prophylaxis or therapy of the abovementioned conditions, the compounds of formula (I) can be used as the compound itself, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as single dose, for example as tablet which may contain from 0.05% to 95% by weight of the active ingredient. Further pharmaceutically active substances may likewise be present, including other compounds of formula (I). The pharmaceutical compositions according to the invention can be produced by one of the known pharmaceutical methods which essentially consist of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Suitable pharmaceutical compositions for parenteral administration comprise preferably sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a special possibility, the active ingredient can be released as described, for example, in Pharmaceutical Research, 2(6): 318 (1986) by electrotransport or iontophoresis.

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished by their low toxicity and their few side effects. The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure. The compounds act as melanocortin receptor agonists and are also suitable for the treatment of disturbances of wellbeing and other psychiatric indications such as, for example, depressions, anxiety states, anxiety neuroses, schizophrenia and for the treatment of disorders associated with the circadian rhythm and for the treatment of drug abuse. They are additionally suitable for the treatment of cancer, arthritis, sleep disorders, sleep apnea, female and male sexual disorders, inflammations, acne, pigmentation of the skin, of metabolic syndrome, disorders of steroid metabolism, skin diseases, psoriasis, mycoses, neurodegenerative diseases, Alzheimer's disease and for lowering alcohol consumption.

In a further aspect of the invention, the compounds of the formula I can be administered in combination with one or more other pharmacologically active substances which are selected, for example, from antidiabetics, antiobesity agents, active ingredients which lower blood pressure, lipid-lowering agents and active ingredients for the treatment and/or prevention of complications caused by diabetes or associated with diabetes.

Suitable antidiabetics include insulins, amylin, derivatives of GLP-1 and GLP-2 such as, for example, those disclosed in WO 98/08871 of Novo Nordisk A/S, and orally active hypoglycemic active ingredients.

The orally active hypoglycemic active ingredients preferably comprise sulfonylureas, biguanidines, meglitinides, oxadiazolidinediones, thiazolidinediones, glucosidase inhibitors, glucagon receptor antagonists, GLP-1 agonists, potassium channel openers such as, for example, those disclosed in WO 97/26265 and WO 99/03861 of Novo Nordisk A/S, insulin sensitizers, activators of insulin receptor kinase, inhibitors of liver enzymes involved in the stimulation of gluconeogenesis and/or glycogenolysis, for example inhibitors of glycogen phosphorylase, modulators of glucose uptake and glucose excretion, compounds which alter lipid metabolism, such as antihyperlipidemic active ingredients and antilipidemic active ingredients, for example HMGCoA reductase inhibitors, inhibitors of cholesterol transport/of cholesterol uptake, inhibitors of bile acid reabsorption or inhibitors of the microsomal triglyceride transfer protein (MTP), compounds which reduce food intake, PPAR and RXR agonists and active ingredients which act on the ATP-dependent potassium channel of the beta cells.

In one embodiment of the invention, the present compounds are administered in combination with insulin.

In a further embodiment, the present compounds are administered in combination with a sulfonylurea such as, for example, tolbutamide, glibenclamide, glimepiride, glipizide, gliquidone, glisoxepide, glibornuride or gliclazide.

In another embodiment, the present compounds are administered in combination with a biguaide such as, for example, metformin.

In yet another embodiment, the present compounds are administered in combination with a meglitinide such as, for example, repaglinide.

In yet a further embodiment, the present compounds are administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In a further embodiment, the present compounds are administered in combination with an α-glucosidase inhibitor such as, for example, miglitol or acarbose.

In another embodiment, the present compounds are administered in combination with an active ingredient which acts on the ATP-dependent potassium channel of the beta cells, such as, for example, tolbutamide, glibenclamide, glimepiride, glipizide, gliclazide or repaglinide.

In yet another embodiment, the present compounds are administered in combination with an antihyperlipidemic active ingredient or an antilipidemic active ingredient such as, for example, cholestyramine, colestipol, clofibrate, fenofibrate, gemfibrozil, lovastatin, pravastatin, simvastatin, atorvastatin, cerivastatin, fluvastatin, probucol, ezetimibe or dextrothyroxine.

In a further embodiment, the present compounds are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

The compounds of the invention may additionally be administered in combination with one or more antiobesity agents or appetite-regulating active ingredients.

Active ingredients of these types may be selected from the group consisting of CART agonists, NPY antagonists, MCH antagonists, orexin antagonists. H3 antagonists, TNF agonists, CRF agonists, CRF BP antagonists, urocortin agonists, β3 agonists, MSH (melanocyte-stimulating hormone) agonists, CCK agonists, serotonin-reuptake inhibitors, mixed serotonin- and noradrenaline-reuptake inhibitors, 5HT modulators, MAO inhibitors, bombesin agonists, galanin antagonists, growth hormone, growth hormone-releasing compounds, TRH agonists, modulators of uncoupling proteins 2 or 3, leptin agonists, dopamine agonists (bromocriptine, Doprexin), lipase/amylase inhibitors, antagonists of cannabinoid receptor 1, modulators of acylation-stimulating protein (ASP), PPAR modulators, RXR modulators, hCNTF agonists or TR-β agonists.

In one embodiment of the invention, the antiobesity agent is leptin or modified leptin.

In another embodiment, the antiobesity agent is dexamphetamine or amphetamine.

In another embodiment, the antiobesity agent is fenfluramine or dexfenfluramine.

In yet another embodiment, the antiobesity agent is sibutramine or the mono- and bisdemethylated active metabolites of sibutramine.

In a further embodiment, the antiobesity agent is orlistat.

In another embodiment, the antiobesity agent is mazindol, diethylpropion or phentermine.

The present compounds may additionally be administered in combination with one or more antihypertensive active ingredients. Examples of antihypertensive active ingredients are beta blockers such as alprenolol, atenol, timolol, pindolol, propranolol and metoprolol, ACE (angiotensin converting enzyme) inhibitors such as, for example, benazepril, captopril, enalapril, fosinopril, lisinopril, quinapril and ramipril, calcium channel blockers such as nifedipine, felodipine, nicardipine, isradipine, nimodipine, diltiazem and verapamil, and alpha blockers such as doxazosin, urapidil, prazosin and terazosin. Reference may furthermore be made to Remington: The Science and Practice of Pharmacy, 19th edition, Gennaro, editor, Mack Publishing Co., Easton, Pa., 1995.

It will be appreciated that every suitable combination of the compounds of the invention with one or more of the aforementioned compounds and optionally one or more other pharmacologically active substances is to be regarded as covered by the scope of protection of the present invention.

The efficacy of the compounds was tested as follows:

Biological Assay:

In Vitro Functional Assays with Recombinant Cells

Function-testing assays were carried out by determining the agonist-induced changes in the intracellular concentration of $Ca^{2+}$ in recombinant HEK293 cells which express both MC4 and G-protein α-16 by means of the FLIPR technique ("Fluorescence Imaging Plate Reader", Molecular Devices Corp.).

For the investigations, cells were seeded into 96-well microtiter plates (50 000 cells/well) and allowed to grow overnight. The medium was removed and the cells were incubated in buffer which contained the fluorescent dye Fluo-4. After this loading with dye, the cells were washed, test substance was added, and changes in the intracellular $Ca^{2+}$ concentration were measured in the FLIPR apparatus. Results have been shown as percentage change relative to the control (0%: no test substance added; 100%: 100 nM reference agonist MTII added), and used to calculate dose/activity plots, with subsequent determination of EC50 values.

| Example | EC50 [nM] |
|---|---|
| 1 | 0.4 |
| 2 | 0.6 |
| 3 | 0.2 |
| 4 | 0.4 |
| 5 | 2 |
| 6 | 3.2 |
| 7 | 2.6 |
| 8 | 2.4 |
| 9 | 1.5 |
| 10 | 5.7 |
| 11 | 0.6 |
| 12 | 0.6 |
| 13 | 4.7 |
| 14 | 1.6 |
| 15 | 30.8 |
| 16 | 717 |
| 17 | 3492 |

Biological Test Model:

The anorectic effect was tested on female NMRI mice. After withdrawal of food for 24 hours, the test product was administered by gavage. The animals were housed singly with free access to drinking water and were offered condensed milk 30 minutes after administration of the product. The condensed milk consumption was determined every half hour for 7 hours, and the general wellbeing of the animals was observed. The measured milk consumption was compared with the vehicle-treated control animals.

TABLE 1

Anorectic effect measured as the reduction in the cumulative milk consumption of treated compared with control animals.

| Example | Oral dose [mg/kg] | Number of animals/ cumulative milk consumption of the treated animals N/[ml] | Number of animals/ cumulative milk consumption of the control animals N/[ml] | Reduction in the cumulative milk consumption as % of the control |
|---|---|---|---|---|
| 1 | 30 | 5 | 5 | 8% |

It is evident from the table that the compounds of the formula I show a good anorectic effect and are thus very suitable as antiobesity agent.

The examples and preparation methods detailed below serve to illustrate the invention without, however restricting it.

General Processes

The starting materials used in the synthesis were purchased from chemical suppliers such as Aldrich, Acros, Sigma, Fluka, Nova Biochem, Advanced Chemtech, Bachem, Lancaster and other companies.

In the synthesis, the functional groups of the amino acid derivatives used were protected by protective groups to prevent side reactions during the coupling steps. Examples of suitable protective groups and their use are described in The Peptides, supra, 1981 and in Vol. 9, Udenfriend and Meienhofer (Editors) 1987 (included herein by reference).

General methods of solid-phase synthesis were used to prepare the compounds of the invention. Methods of this type are described for example by Steward and Young in Solid Phase Peptide Synthesis (Freeman & Co., San Francisco 1969) (included herein by reference).

Unless indicated otherwise, the compounds were synthesized using TentaGel HL12019 Resin (Rapp Polymere, Tübingen). This commercially available polymer contains a bromoacetal linker. This type of coupling can be incorporated in all types of hydroxy-tentagel by the process described by Vojkovsky, T. et al., J. Org. Chem. 1998, 63, 3162-3163, and Patek, M., Contribution to Combinatorial Chemistry 2000, London, 11.-14.7. 2000 (included herein by reference).

In the first synthesis step (see scheme 1 for general synthetic scheme), amine was used in DMSO to replace bromine in the bromoacetal link at an elevated temperature. Fmoc-protected amino acid was coupled onto the secondary amine produced thereby on the polymer. The coupling was effected by means of DIC/HOAt or HATU/DIEA, usually in DMF. The coupling was carried out at room temperature (RT) for 16 hours or at 55° C. for 4-5 hours. Protection by the Fmoc group was eliminated by using 50% piperidine in DMF (5+15 minutes). The substitution can be determined by measuring the amount of liberated Fmoc from the absorbance of the solution at 302 nm after elimination of the protection, the volume of the washing liquid and the weight of the polymer employed in the synthesis in accordance with the description in Krchnak, V. et al., Collect. Czech. Chem. Commun. 53 (1988) 2542 (incorporated herein by reference).

The free amino group of the structure bound to the solid phase was then coupled to Fmoc-beta-alanine (or Fmoc-alpha-amino acid or substituted beta-amino acid). The coupling was effected with N,N'-diisopropylcarbodiimide (DIC) in the presence of HOBt, usually in DMF. The completeness of the coupling was monitored by the ninhydrin test.

A protection by the Fmoc group was eliminated with 50% piperidine in DMF for 5+15 minutes. The amount of liberated Fmoc was measured from the absorbance of the solution at 302 nm after elimination of the protection, the volume of the washing liquid and the weight of the polymer employed in the synthesis.

The free amino groups of the structure bound to the solid phase was then sulfonylated with up to 2 equivalents of a suitable sulfonyl chloride/DIEA in DCM or acetonitrile.

The completeness of the sulfonylation was monitored by the ninhydrin test.

After completion of the assembly of the precursor of the linear compound on the polymer, the solid phase washed successively with DMF and DCM or THF and dried in vacuo.

The desired compound was subjected to cyclative cleavage off with formic acid at room temperature for 18-24 hours, at 50° C. for 6 hours or by a combination of the two conditions. The polymer was filtered off and washed with DCM or formic acid. The washing liquid was introduced into the formic acid solution. The solution was evaporated. The residue was dissolved in a mixture of water and acetonitrile and freeze dried.

The dried compound was purified with HPLC with a suitable gradient of 0.1% TFA in water and acetonitrile (ACN). After collection of the peak containing the desired synthetic product, the solution of the compound was freeze dried. To confirm that the correct compound had been synthesized, the compound was subjected to a qualitative determination with electrospray mass spectrum (LC/MS) and/or an NMR analysis.

For HPLC analysis a sample of the compound was analyzed with the Beckman HPLC system (consisting of the solvent supply system 126, the programmable detector module 166 and the autosampler 507e and controlled by data station with Gold Nouveau software) using a YMC ODS-AM 4.6×250 mm column (S-5 (5 μm), YMC, Inc. Wilmington, N.C. USA) at 230 nm. With this setting, a flow rate of 1 ml/min was used and a gradient of water/0.1% TFA buffer and ACN(HPL quality) was used as eluent.

Scheme 1:

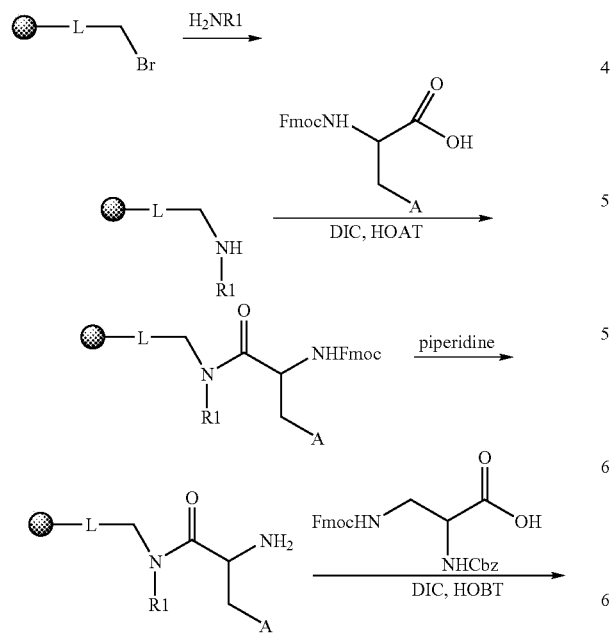

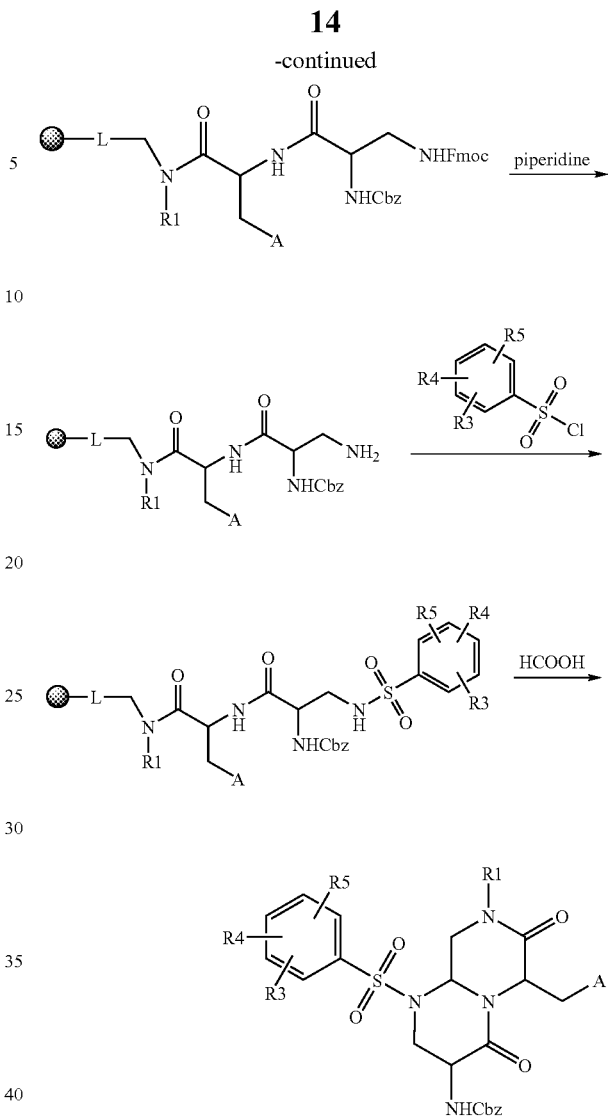

The compounds can also be prepared in solution in analogy to the described synthesis on the resin. (Scheme 2). In place of the functionalized resin, in the first stage 2-bromo-1,1-diethoxyethane is reacted with a primary amine.

Scheme 2:

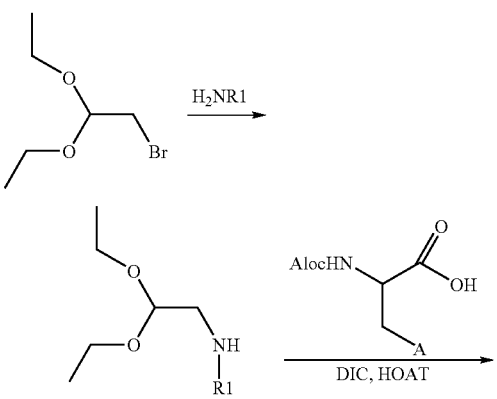

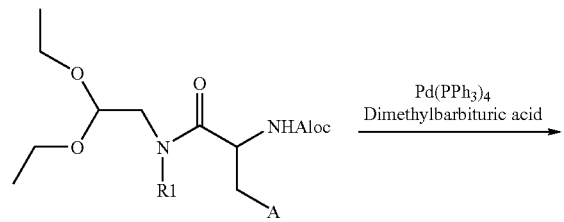

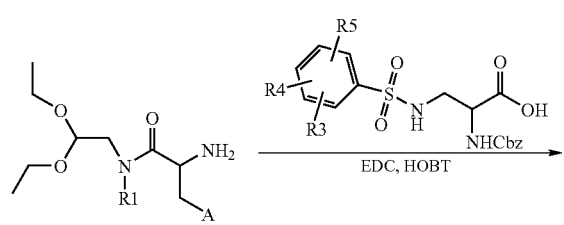

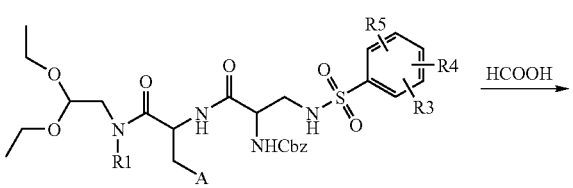

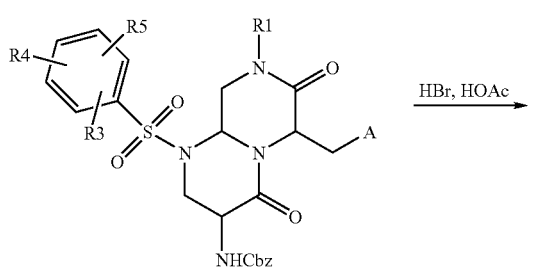

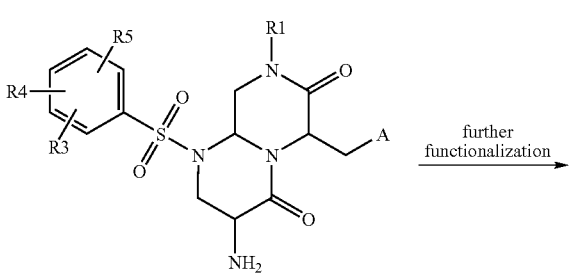

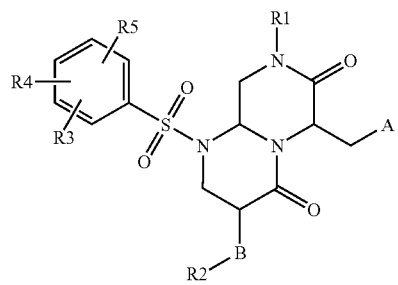

The resulting product is reacted with the amino acid in analogy to the solid-phase synthesis. The allyloxycarbonyl protective group (Aloc) can be used in place of FMOC as amino-protective group for the amino acid, and is introduced (Aloc-Cl, triethylamine) and eliminated (Pd(PPh$_3$)$_4$, dimethylbarbituric acid) by methods known from the literature.

Unlike in the solid phase synthesis, the protected amino carboxylic acid is converted into the sulfonamide using the sulfonyl chloride in the presence of triethylamine. The free carboxylic acid is coupled by the carbodiimide method (EDC, HOBt) or with use of uronium salts (HATU, HOAt) to the free amine which has been obtained by elimination of the Aloc group.

The cyclization proceeds under acidic conditions and the benzyloxycarbonyl (Cbz) group is eliminated with HBr in glacial acid.

Subsequent functionalizations are carried out by coupling with carboxylic acids using PyBOP (benzotriazol-1-yloxytris (pyrrolidino)phosphonium hexafluorophosphate), HOAt in the presence of triethylamine in DMF.

The product was purified by developing a sample of the freeze-dried crude substance in a mixture of 0.1% strength aqueous TFA with 10-50% acetonitrile or in acetic acid. The solution of the compound was usually filtered through a syringe connected to an ACRODISC 13 CR PTFE 0.45 μm filter (Gelman Sciences; Ann Arbor, Mich., USA). An appropriate volume of the filtered solution of the compound was injected into a semipreparative C 18 column (YMC ODS-AM, S-5 (5 μm), 20×150 mm, YMC, Inc., Wilmington, N.C., USA). The flow rate of the gradient of water/0.1% TFA buffer and ACN (HPL quality) as eluent was maintained by means of the Beckman SYSTEM GOLD HPLC (System Gold, programmable solvent module 126 and programmable detector module 166, controlled by SYSTEM GOLD software). Elution of the compound was monitored by UV detection at 220 or 254 nm. After identification of the peak of the compound to be synthesized by LC/MS, the compound was collected, freeze dried and subjected to biological testing.

After purification, compounds with basic groups were obtained as trifluoroacetates. Hydrochlorides of these compounds can easily be prepared by treating the trifluoroacetate of the compound with an excess of HCl/dioxane. After evaporation of the solvents, the hydrochloride of the compound was precipitated with diethyl ether and isolated by filtration.

LC/MS was carried out with PE Sciex API 150EX and Sciex MassChrom software, equipped with a Gilson 215 liquid handler, two Shimadzu LC-10AD liquid modules, a Shimadzu SPD-10A detector, a Keystone Betasil C-18 column (2×30 mm, 3 μm, flow rate of the acetonitrile/water/0.1% TFA gradient 0.7 ml/min) in ES+mode.

For the NMR analysis, the samples were measured in DMSO-d$_6$ (Aldrich) with a Bruker Avance DPX 300.

Scheme 3:

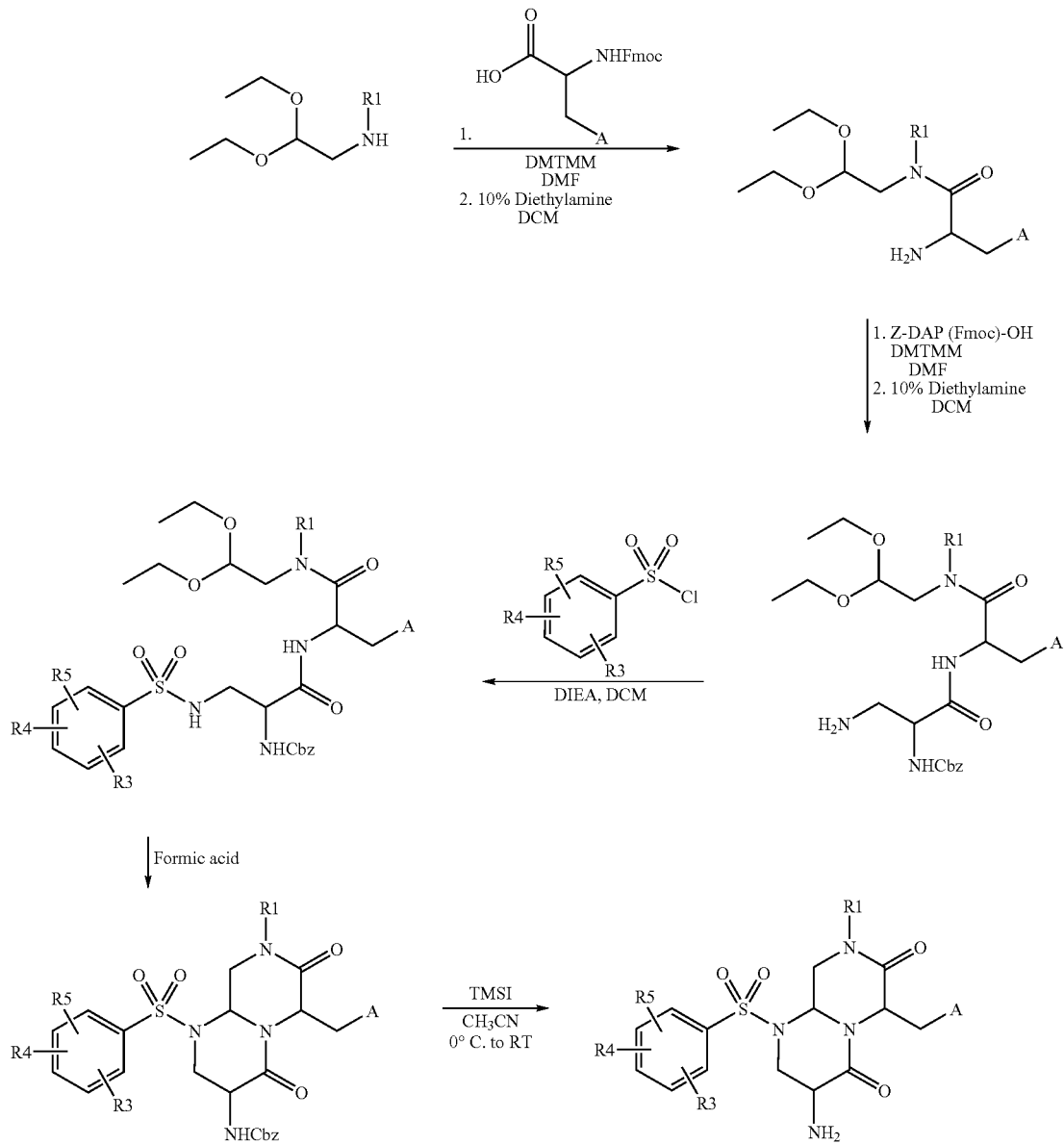

The synthesis shown in Scheme 3 was carried out in analogy to the other solution synthesis. In this case, the amide couplings were carried out in each case with DMTMM as coupling reagent. In addition, Fmoc was employed as protective group in the solid-phase chemistry, and was eliminated again with diethylamine. The sulfonamide was not introduced along with the second amide coupling, but was formed after the latter with use of diethylamine as base. The cyclization was carried out in analogy to the procedure described above. The Cbz group was eliminated with TMSI in acetonitrile. All further functionalizations were performed in analogy to the above description.

The reagents and building blocks used in the syntheses originated from various suppliers such as Aldrich, Acros, Sigma, Fluka, Nova Biochem, Advanced Chemtech, Bachem, Lancaster, Rapp Polymere etc.

Unless indicated otherwise, the following methods were used for the chemical analysis: liquid chromatography/mass spectrometry analysis (LC/MS): Agilent 1100 LC with mass spectrometer detector. The following were used: Waters (YMC) Combiscreen Pro C18 4.6×33.5μ, 120 A, 3 minutes with 10% acetonitrile (0.1% trifluoroacetic acid) and 90% water (0.1% trifluoroacetic acid) to 0% acetonitrile (0.1% trifluoroacetic acid) and 100% water (0.1% trifluoroacetic acid). 1-minute flow-through time and subsequently 1-minute equilibration to the starting conditions.

Electrospraying mass spectrometry, positive mode (unless indicated otherwise).

Preparative LC: semipreparative liquid chromatograms were recorded with a Gilson 215 liquid handler, an apparatus which is suitable for analyses and semipreparative processes.

Mobile phase: water (0.1% TFA) and acetonitrile (0.1% TFA). The samples were initially investigated by analytical methods. An appropriate semipreparative process was then used. 5% to 100% acetonitrile, 12 minutes (unless indicated otherwise). Waters (YMC) Combiscreen columns for analysis, 4.6×50 per C18, 5μ, 120 A are used. Waters Combiscreen 20×50.5μ, 120 A semipreparative columns.

Thin-layer chromatograms (TLC) were recorded with glass-reinforced 60F-254 silica gel plates 0.25 mm thick.

Flash chromatography: this process was carried out by the method described by Still, W. C., Kahn, M. and Mitra, A. in J. Org. Chem. 1978, 43, 2923, or adapted to commercially available systems such as Biotage Horizon, Isco Opix or Companion. The solvent systems indicated in the experimental examples were used in these cases.

Microwave synthesis: unless indicated otherwise, the microwave reactions were carried out in a personal chemistry creator, optimizer or synthesizer.

All the calculated masses indicated are monoisotopic.

Abbreviations

Unless indicated otherwise, the abbreviations in the examples below have the following meaning:

ACN Acetonitrile

Aloc=Allyloxycarbonyl

DIC Diisopropylcarbodiimide

EDC=1-(3-Dimethylaminopropyl)-3-ethylcarbodiimide

FMOC=9-Fluorenylmethyloxycarbonyl

DCE=1,2-Dichloroethane

DEA=Diethylamine

DIEA=Diisopropylethylamine $NaBH_3CN$=Sodium cyanoborohydride

DMAP=N,N-Dimethylaminopyridine

DMF=N,N-Dimethylfoimamide

THF=Tetrahydrofuran

DIC=Diisopropylcarbodiimide

DMSO=Dimethyl sulfoxide

DCM=Dichloromethane (also referred to as methylene chloride)

DMTMM=4-(4,6-Dimethoxy[1,3,5]triazin-2-yl]-4-methyl-morpholinium chloride HOBt=1-Hydroxybenzotriazole HOAt=1-Hydroxy-7-azabenzotriazole HATU=Dimethylamino([1,2,3]triazolo[4,5-b]pyridin-3-yloxy)methylenedimethyl-ammonium hexafluorophosphate EtOAc=Ethyl acetate HOAc=Acetic acid $Et_3N$=Triethylamine HCl=Hydrochloric acid HBr=Hydrobromic acid HPLC=High performance liquid chromatography PyBOP=Benzotriazol-1-yloxytris(pyrrolidino)phosphonium hexafluorophosphate TEA=Triethylamine TMSI=Trimethylsilyl iodide The following examples serve to explain the invention in more detail without restricting it to the products and embodiments described in the examples.

Example 1

N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-amino-3-methylbutyryl)pyrrolidin-2-carboxamide

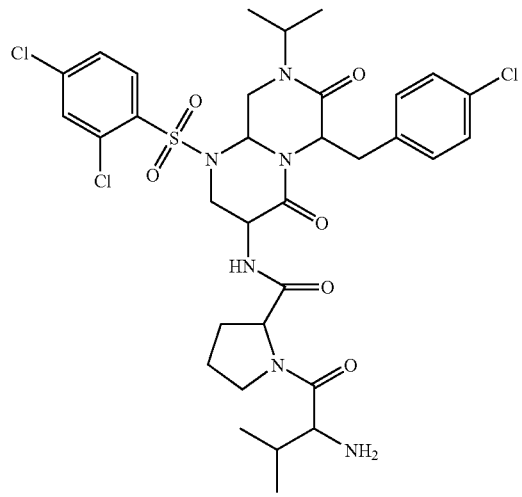

Method A:

a) 2-Allyloxycarbonylamino-3-(4-chlorophenyl)propionic acid

The product is prepared by methods ($ET_3N$, methanol) known from the literature starting from 10 g of 4-chlorophenylalanine and 8 ml of allyl chloroformate. MW=283.71 (calculated monoisotopic); measured value $(M+H)^+$: 284.1.

b) Allyl {2-(4-chlorophenyl)-1-[(2,2-diethoxyethyl)isopropylcarbamoyl]ethyl}-carbamate 7.8 ml of DIC are added dropwise to a solution of 5.7 g of 2-allyloxycarbonylamino-3-(4-chlorophenyl)propionic acid, 3.5 g of (2,2-diethoxyethyl)isopropylamine, 6.8 g of HOAt in 30 ml of DMF and the solution is stirred for 12 h. The reaction solution is concentrated under reduced pressure and purified by flash chromatography on silica gel (eluent ethyl acetate/n-heptane=1/3). The desired product is obtained with MW=440.97 (calculated monoisotopic); measured value $(M+H)^+$: 441.15 c) 2-Amino-3-(4-chlorophenyl)-N-(2,2-diethoxyethyl)-N-isopropylpropionamide 10 mg of palladium tetrakistriphenylphosphine are added to a solution of 13.2 g of allyl {2-(4-chlorophenyl)-1-[(2,2-diethoxyethyl)isopropylcarbamoyl]ethyl}carbamate, 18.9 g of dimethylbarbituric acid in 140 ml of methylene chloride under a protective argon gas atmosphere, and the reaction mixture is stirred for 12 h at room temperature. The reaction solution is concentrated under reduced pressure and purified by flash chromatography on silica gel (eluent methylene chloride, 1% Et₃N, 0-10% methanol). The desired product is obtained with MW=356.90 (calculated monoisotopic); measured value $(M-C_2H_6O+H)^+$: 311.10 d) 2-Benzyloxycarbonylamino-3-(2,4-dichlorobenzenesulfonylamino)-propionic acid A solution of 3.8 g of 2,4-dichlorobenzenesulfonyl chloride in 5 ml of dioxane is added dropwise to a solution of 2.3 g of 3-amino-2-benzyloxycarbonylamino-propionic acid in 20 ml of 1N NaOH solution. The reaction mixture is left to stir while controlling the pH (pH>7) for 12 h, the pH is reduced below 7 by adding citric acid, and the reaction solution is then extracted with methylene chloride. The organic phase is dried over magnesium sulfate, concentrated under reduced pressure and employed without further purification in the next reaction step.

The desired product is obtained with MW=446.01 (calculated monoisotopic); measured value $(M+H-CO_2)^+$: 403.00.

e) N-{2-(4-Chlorophenyl)-1-[(2,2-diethoxyethyl)isopropylcarbamoyl]ethyl}-3-(2,4-dichlorobenzenesulfonylamino)-2-methanesulfonylaminopropionamide 52 mg of EDC, 45 mg of HOBt and 100 µl of N-ethylmorpholine are added to a solution of 124 mg of 2-benzyloxycarbonylamino-3-(2,4-dichlorobenzenesulfonylamino)propionic acid in 1 ml of DMF. A solution of 100 mg of 2-amino-3-(4-chlorophenyl)-N-(2,2-diethoxyethyl)-N-isopropylpropionamide in 1 ml of DMF is added dropwise thereto, and the solution is left to stir for 12 h. The reaction solution is filtered, mixed with ethyl acetate and then extracted with 5% aqueous sodium bicarbonate solution and aqueous sodium chloride solution. Drying of the organic phase over sodium sulfate is followed by concentration under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=784.186 (calculated); measured value $(M-CO_2+H)^+$: 741.10.

f) Benzyl [6-(4-chlorobenzyl)-1-(2,4-dichlorobenzenesulfonyl)-8-isopropyl-4,7-dioxooctahydropyrazino[1,2-a]pyrimidin-3-yl]carbamate A solution of 218 mg of benzyl (2-(2,4-dichlorobenzenesulfonylamino)-1-{2-(4-chlorophenyl)-1-[(2,2-diethoxyethyl)isopropylcarbamoyl]ethylcarbamoyl}ethyl)carbamate in 3 ml of formic acid is stirred at room temperature for 12 h and then at 55° C. for 5 h. The reaction solution is concentrated under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=692.10 (calculated monoisotopic); measured value $(M+H)^+$: 693.05.

g) 3-Amino-6-(4-chlorobenzyl)-1-(2,4-dichlorobenzenesulfonyl)-8-isopropyl-hexahydropyrazino[1,2-a]pyrimidine-4,7-dione A solution of 79 mg of benzyl [6-(4-chlorobenzyl)-1-(2,4-dichlorobenzenesulfonyl)-8-isopropyl-4,7-dioxooctahydropyrazino[1,2-a]pyrimidin-3-yl]carbamate in 2 ml of a 33% solution of HBr in glacial acetic acid is stirred for 2 h. The reaction solution is mixed with aqueous sodium carbonate solution and extracted with ethyl acetate. The organic phase is dried over magnesium carbonate and concentrated under reduced pressure, and the residue is separated by HPLC (Knauer Eurospher-100-10-C18, water (0.1% trifluoroacetic acid)/acetonitrile (0.1% trifluoroacetic acid)=80/20→10/90). The desired product is obtained with MW=558.07 (calculated monoisotopic); measured value $(M+H)^+$: 559.10.

h) N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-amino-3-methylbutyryl)pyrrolidine-2-carboxamide A solution of 100 mg of 3-amino-6-(4-chlorobenzyl)-1-(2,4-dichlorobenzenesulfonyl)-8-isopropylhexahydropyrazino[1,2-a]pyrimidine-4,7-dione, 56.3 mg of 1-(2-tert-butoxycarbonylamino-3-methylbutyryl)pyrrolidine-2-carboxylic acid in 680 µl of DMF is cooled to 0° C. and 103.6 mg of PyBOP, 25.2 mg of HOAt and 72 µl of Et₃N are added. The solution is stirred at 0° C. for 10 min and then at room temperature for 4 h. The solvent is removed in vacuo. The residue is then taken up in ethyl acetate and water. The aqueous phase extracted twice with ethyl acetate. The combined organic phases dried over Na₂SO₄ and the solvent removed in vacuo. The product is then mixed with 1 ml of a 4 molar HCl/dioxane solution, and the mixture is stirred at room temperature for 6 h. The solvent is then removed in vacuo. The crude product is separated by HPLC (Waters-Xterra™ MS C18, 5 µm, water (0.1% trifluoroacetic acid)/acetonitrile (0.1% trifluoroacetic acid)=80/20→10/90).

The desired product is obtained with MW=754.19 (calculated, monoisotopic); measured value $(M+H)^+$: 755.45.

Method B a) 9H-Fluoren-9-ylmethyl {2-(4-chlorophenyl)-1-[(2,2-diethoxyethyl)isopropylcarbamoyl]ethyl}carbamate 210 mg (1.2 mmol) of (2,2-diethoxyethyl)isopropylamine and 376 mg (1.20 mmol) of DMTMM are added to a solution of 505 mg (1.2 mmol) of N-Fmoc-4-Cl-Phe-OH in 2 ml of DMF. The reaction mixture is stirred at room temperature overnight. It is then extracted with 40 ml of diethyl ether and washed with 10 ml of water. The combined organic phases are dried over MgSO₄ and concentrated in vacuo. The crude product is purified by chromatography on 10 g SiO₂ (eluent DCM followed by 20% EtOAc/DCM). 530 mg of the desired product are obtained as an oil. MW=578.26 (calculated, monoisotopic); measured value $(M+H)^+$: 579 b) 2-Amino-3-(4-chlorophenyl)-N-(2,2-diethoxyethyl)-N-isopropylpropionamide

A solution of 530 mg (0.915 mmol) of 3-(4-chlorophenyl)-N-(2,2-diethoxyethyl)-N-isopropyl-2-methylpropionamide in 15 ml of a 20% diethylamine DCM solution is stirred at room temperature overnight. The reaction mixture is concentrated in vacuo and purified by chromatography on 5 g of SiO₂ (eluent DCM followed by 20% EtOAc/DCM followed by 20% MeOH/DCM). 320 mg of the desired product are obtained as an oil. MW=356.19 (calculated, monoisotopic); measured value $(M+H)^+$=357 c) 9H-Fluoren-9-ylmethyl (2-benzyloxycarbonylamino-2-{2-(4-chlorophenyl)-1-[(2,2-diethoxyethyl)isopropylcarbamoyl]ethylcarbamoyl}ethyl)carbamate Z-Dap-Fmoc-OH was coupled with 2-amino-3-(4-chlorophenyl)-N-(2,2-diethoxyethyl)-N-isopropylpropionamide under the same conditions as described under a). The desired product is obtained with MW=798.34 (calculated, monoisotopic); measured value (M+Na)$^+$=821.43 d) Benzyl (2-amino-1-{2-(4-chlorophenyl)-1-[(2,2-diethoxyethyl)isopropylcarbamoyl]-ethylcarbamoyl}ethyl)carbamate The Fmoc protective group is eliminated from 9H-fluoren-9-ylmethyl (2-benzyloxycarbonylamino-2-{2-(4-chlorophenyl)-1-[(2,2-diethoxyethyl)isopropylcarbamoyl] ethylcarbamoyl}ethyl)carbamate using diethylamine and employing the method as described under b). The desired product is obtained with MW=576.27 (calculated, monoisotopic); measured value (M+H)$^+$=577.22 e) Benzyl [1-{2-(4-chlorophenyl)-1-[(2,2-diethoxyethyl)isopropylcarbamoyl]-ethylcarbamoyl}-2-(2,4-dichlorobenzenesulfonylamino)ethyl]carbamate 1.94 ml (11.09 mmol) of DIEA and 1.5 g (6.1 mmol) of 2,4-dichlorophenylsulfonyl chloride are added to a solution of 3.2 g (5.54 mmol) of benzyl (2-amino-1-{2-(4-chlorophenyl)-1-[(2,2-diethoxyethyl)isopropylcarbamoyl] ethylcarbamoyl}ethyl)carbamate in 75 ml of DCM. The solution is stirred at room temperature overnight. The solution is then concentrated in vacuo, and the residue is purified by column chromatography on 100 g of SiO$_2$ (eluent DCM followed by 20% EtOAc/DCM). 2.78 g of the desired product are obtained as a colorless foam. MW=784.19 (calculated, monoisotopic); measured value (M+Na)$^+$=807.24 f) Benzyl [6-(4-chlorobenzyl)-1-(2,4-dichlorobenzenesulfonyl)-8-isopropyl-4,7-dioxooctahydropyrazino[1,2-a]pyrimidin-3-yl]carbamate A solution of 2.74 (3.49 mmol) of benzyl [1-{2-(4-chlorophenyl)-1-[(2,2-diethoxyethyl)isopropylcarbamoyl]ethylcarbamoyl}-2-(2,4-dichlorobenzenesulfonylamino)ethyl]-carbamate in 45 ml of formic acid is heated at 60° C. for 6 h. The reaction mixture is then concentrated in vacuo, and the residue is purified by chromatography on 40 g of SiO$_2$ (eluent DCM followed by 20% EtOAc/DCM). 2.25 g of the cyclized compound are obtained as a colorless solid.

LC/MS MW=692.1 (calculated, monoisotopic); measured value (M+H)$^+$=693 g) 3-Amino-6-(4-chlorobenzyl)-1-(2,4-dichlorobenzenesulfonyl)-8-isopropylhexahydropyrazino[1,2-a]pyrimidine-4,7-dione 206 ml (1.44 mmol) of trimethylsilyl iodide (TMSI) are added to a solution of 250 mg (0.36 mmol) of benzyl [6-(4-chlorobenzyl)-1-(2,4-dichlorobenzenesulfonyl)-8-isopropyl-4,7-dioxooctahydropyrazino[1,2-a]pyrimidin-3-yl]carbamate in 10 ml of CH$_3$CN at 0° C. The reaction solution is allowed to reach room temperature and is stirred at this temperature for 2 h. 5 ml of MeOH are added to the reaction solution, and then the solution is concentrated in vacuo. The residue is purified on a 5 g SCX cartridge (eluted with MeOH followed by 3N NH$_3$/MeOH). 185 mg of the desired compound are obtained as a white powder. LC/MS 558.07 (calculated, monoisotopic); measured value (M+H)$^+$: 559.10 h) N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-amino-3-methylbutyryl) pyrrolidine-2-carboxamide Synthesis takes place as described in Method A (step 1h).

Example 2

N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-aminoacetyl)pyrrolidine-2-carboxamide

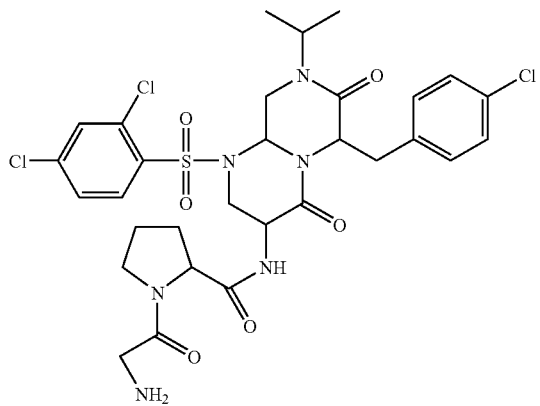

Synthesis took place in analogy to Example 1 using 1-(2-tert-butoxycarbonylamino-acetyl)pyrrolidine-2-carboxylic acid in step 1h). The desired product was obtained with MW=712.14 (calculated, monoisotopic); measured value (M+H)$^+$: 713.2.

Example 3

N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-aminopropionyl)pyrrolidine-2-carboxamide

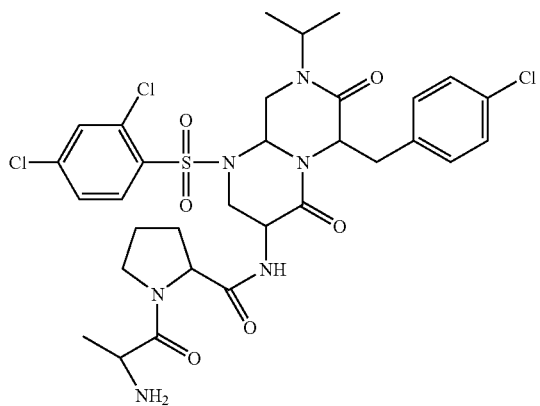

Synthesis took place in analogy to Example 1 using 1-(2-tert-butoxycarbonylamino-propionyl)pyrrolidine-2-carboxylic acid in step 1h). The desired product was obtained with MW=726.16 (calculated, monoisotopic); measured value (M+H)+: 727.22.

Example 4

N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-amino-4-methylpentanoyl)pyrrolidine-2-carboxamide

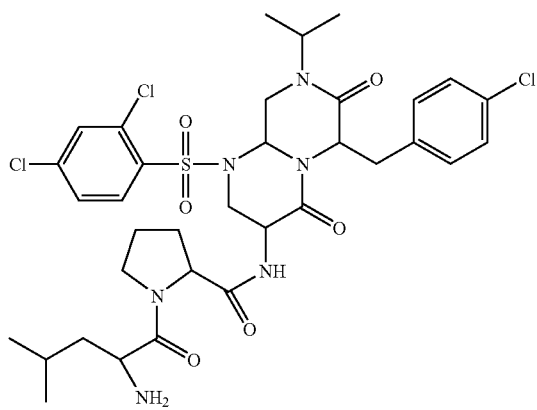

Synthesis took place in analogy to Example 1 using 1-(2-tert-butoxycarbonylamino-4-methylpentanoyl)pyrrolidine-2-carboxylic acid in step 1h). The desired product was obtained with MW=768.20 (calculated, monoisotopic); measured value (M+H)+: 769.27.

Example 5

N-[6-(4-Chlorobenzyl)-1-(2,4-dichlorobenzenesulfonyl)-8-isopropyl-4,7-dioxooctahydropyrazino[1,2-a]pyrimidin-3-yl]-1-(2-dimethylamino-3-methylbutyryl)pyrrolidine-2-carboxamide

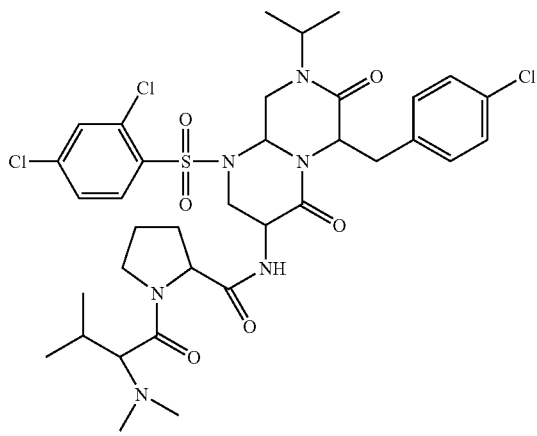

15 µl of formaldehyde, 15 µl of glacial acetic acid and 62.8 µl of a 1M sodium cyanoborohydride solution in THF are added to a solution of 40 mg of N-[6-(4-chlorobenzyl)-1-(2,4-dichlorobenzenesulfonyl)-8-isopropyl-4,7-dioxooctahydropyrazino[1,2-a]pyrimidin-3-yl]-1-(2-amino-3-methylbutyryl)pyrrolidine-2-carboxamide in 556 µl of methanol and 278 µl of methylene chloride. The reaction mixture is stirred at room temperature for 6 h. The solvent is then removed in vacuo, and the residue is taken up in ethyl acetate and water. The aqueous phase is extracted twice with ethyl acetate, and the combined organic phases are dried over sodium sulfate and filtered, and the solvent is removed in vacuo. The resulting crude product is separated by HPLC (Knauer Eurospher-100-10-C18, water (0.1% trifluoroacetic acid)/acetonitrile (0.1% trifluoroacetic acid)=80/20→10/90). The desired product is obtained with MW=782.22 (calculated, monoisotopic); measured value (M+H)+: 783.35.

Example 6

N-[6-(4-Chlorobenzyl)-1-(2-chloro-5-fluorobenzenesulfonyl)-8-isopropyl-4,7-dioxooctahydropyrazino[1,2-a]pyrimidin-3-yl]-1-(2-amino-3-methylbutyryl)pyrrolidine-2-carboxamide

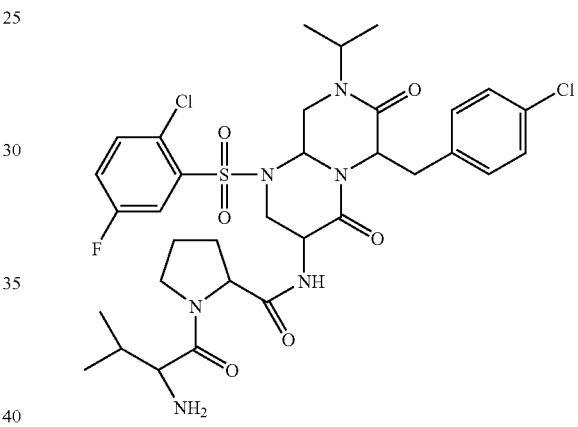

a) 2-Chloro-5-fluorobenzenesulfonyl chloride 5 g (34.3 mM) of 2-chloro-5-fluoroaniline were slowly added to a solution of 17 ml of concentrated hydrochloric acid solution and 11 ml of water at 0° C. The reaction mixture is stirred at 0° C. for 1 hour. Addition of 2.49 g (36.1 mM) of $NaNO_2$ in 6 ml of $H_2O$ is followed by stirring the mixture at 0° C. for 15 minutes and then adding to a solution of 692 mg (5.15 mM) of sulfur dioxide and copper(II) chloride in 10 ml of acetic acid. The reactants were stirred at 0° C. for 15 minutes and then at room temperature for a further 15 minutes. The reaction mixture is extracted with EtOAc. The organic phase is concentrated, dissolved in EtOAc, washed with 1N $NaHCO_3$ solution, dried over $MgSO_4$ and concentrated. 7.86 g of the desired sulfonyl chloride are obtained as a yellow oil.

b) Benzyl (2-(2-chloro-5-fluorobenzenesulfonylamino)-1-{2-(4-chlorophenyl)-1-[(2,2-diethoxyethyl)isopropylcarbamoyl]ethylcarbamoyl}ethyl) carbamate $Et_3N$ is added to a solution of 800 mg (1.39 mM) of the amine benzyl (2-amino-1-{2-(4-chlorophenyl)-1-[(2,2-diethoxyethyl)isopropylcarbamoyl]ethylcarbamoyl}ethyl)carbamate in 4 ml of DCM. The sulfonyl chloride prepared as described above (476 mg, 2.08 mM) in solution in 3 ml of DCM is then added at room temperature. The reaction mixture is stirred at room temperature for 1 hour and washed with 1N NaHCO₃. The organic phase is dried on MgSO₄ and concentrated. The residue is chromatographed on 40 g of SiO₂ (elution with 30-70% EtOAc in heptane). 860 mg of the desired substance is taken as a white solid. LC/MS: MG (calculated, monoisotopic)=769.72; measured value (M+Na)= 791.

c) Benzyl [6-(4-chlorobenzyl)-1-(2-chloro-5-fluorobenzenesulfonyl)-8-isopropyl-4,7-dioxooctahydropyrazino[1,2-a]pyrimidin-3-yl]carbamate Synthesis takes place in analogy to Example 1f) (Method B) starting from N-{2-(4-chlorophenyl)-1-[(2,2-diethoxyethyl)isopropylcarbamoyl]ethyl}-3-(2-chloro-5-fluorobenzenesulfonylamino)-2-methanesulfonylaminopropionamide. The desired product is obtained when MW=676.13 (calculated, monoisotopic); measured value (M+H)⁺: 677.16 d) 3-Amino-6-(4-chlorobenzyl)-1-(2-chloro-5-fluorobenzenesulfonyl)-8-isopropylhexahydropyrazino[1,2-a]pyrimidine-4,7-dione Synthesis takes place in analogy to Example 1g) (Method B) starting from benzyl [6-(4-chlorobenzyl)-1-(2-chloro-5-fluorobenzenesulfonyl)-8-isopropyl-4,7-dioxooctahydropyrazino[1,2-a]pyrimidin-3-yl]carbamate. The desired product is obtained with MW=542.1 (calculated, monoisotopic); measured value (M+H)⁺: 543.10 e) N-[6-(4-Chlorobenzyl)-1-(2-chloro-5-fluorobenzenesulfonyl)-8-isopropyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(4-chlorobenzyl)-1-(2-chloro-5-fluorobenzenesulfonyl)-8-isopropylhexahydropyrazino[1,2-a]pyrimidine-4,7-dione. The desired product is obtained with MW=738.22 (calculated, monoisotopic); measured value (M+H)⁺: 739.20.

Example 7

N-[6-(4-Chlorobenzyl)-1-(2-chloro-4-trifluoromethoxybenzene-sulfonyl)-8-isopropyl-4,7-dioxooctahydropyrazino[1,2-a]-pyrimidin-3-yl]-1-(2-amino-3-methylbutyryl)pyrrolidine-2-carboxamide

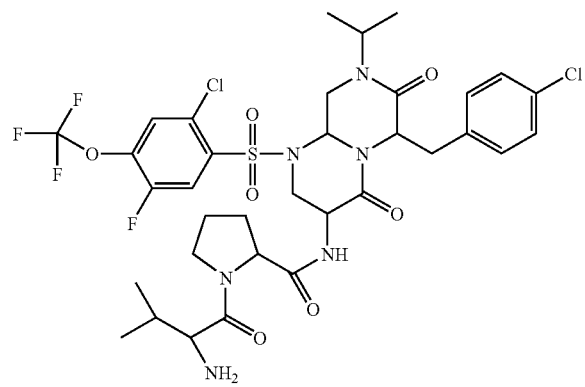

a) 2-Chloro-4-trifluoromethoxybenzenesulfonyl chloride

2-Chloro-4-trifluoromethoxyaniline is reacted to give the corresponding sulfonyl chloride by the same protocol as in Example 6a).

b) Benzyl [1-{2-(4-chlorophenyl)-1-[(2,2-diethoxyethyl)isopropylcarbamoyl]ethylcarbamoyl}-2-(2-chloro-4-trifluoromethoxybenzenesulfonylamino)ethyl]carbamate Synthesis takes place in analogy to Example 6b) starting from 2-chloro-4-trifluoromethoxybenzenesulfonyl chloride. The desired product is obtained with MW=834.21 (calculated, monoisotopic); measured value (M+Na)⁺: 857.0 c) Benzyl [6-(4-chlorobenzyl)-1-(2-chloro-4-trifluoromethoxybenzenesulfonyl)-8-isopropyl-4,7-dioxooctahydropyrazino[1,2-a]pyrimidin-3-yl]carbamate Synthesis takes place in analogy to Example 1f) (Method B) starting from N-{2-(4-chlorophenyl)-1-[(2,2-diethoxyethyl)isopropylcarbamoyl]ethyl}-3-(2-chloro-4-trifluoromethoxybenzenesulfonylamino)-2-methanesulfonylaminopropionamide. The desired product is obtained with MW=742.12 (calculated, monoisotopic); measured value (M+H)⁺: 743.14 d) 3-Amino-6-(4-chlorobenzyl)-1-(2-chloro-5-trifluoromethoxybenzenesulfonyl)-8-isopropylhexahydropyrazino[1,2-a]pyrimidine-4,7-dione Synthesis takes place in analogy to Example 1g) (Method B) starting from benzyl [6-(4-chlorobenzyl)-1-(2-chloro-4-trifluoromethoxybenzenesulfonyl)-8-isopropyl-4,7-dioxooctahydropyrazino[1,2-a]pyrimidin-3-yl]carbamate. The desired product is obtained with MW=608.09 (calculated, monoisotopic); measured value (M+H)⁺: 609.07.

e) N-[6-(4-Chlorobenzyl)-1-(2-chloro-4-trifluoromethoxybenzenesulfonyl)-8-isopropyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(4-chlorobenzyl)-1-(2-chloro-4-trifluoromethoxybenzenesulfonyl)-8-isopropylhexahydropyrazino[1,2-a]pyrimidine-4,7-dione. The desired product is obtained with MW=804.21 (calculated, monoisotopic); measured value (M+H)⁺: 805.21.

Example 8

N-[6-(4-Chlorobenzyl)-1-(4-chloro-2-fluorobenzene-sulfonyl)-8-isopropyl-4,7-dioxooctahydropyrazino[1,2-a]pyrimidin-3-yl]-1-(2-amino-3-methylbutyryl)pyrrolidine-2-carboxamide

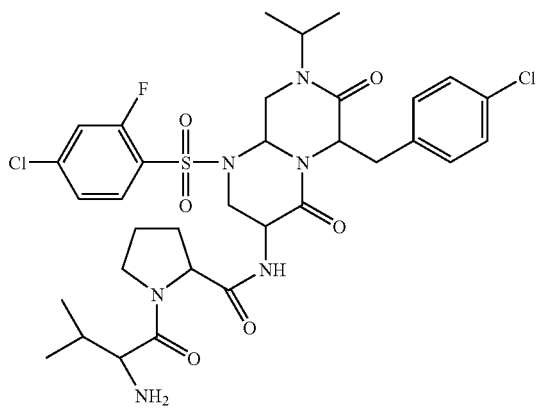

a) Benzyl [1-{2-(4-chlorophenyl)-1-[(2,2-diethoxyethyl)isopropylcarbamoyl]ethylcarbamoyl}-2-(4-chloro-2-fluorobenzenesulfonylamino)ethyl]carbamate Synthesis takes place in analogy to Example 6b) starting from 4-chloro-2-fluorobenzenesulfonyl chloride. The desired product is obtained with MW=768.22 (calculated, monoisotopic); measured value (M+Na)+: 791.0 b) Benzyl [6-(4-chlorobenzyl)-1-(4-chloro-2-fluorobenzenesulfonyl)-8-isopropyl-4,7-dioxooctahydropyrazino[1,2-a]pyrimidin-3-yl]carbamate Synthesis takes place in analogy to Example 1f) (Method B) starting from N-{2-(4-chlorophenyl)-1-[(2,2-diethoxyethyl)isopropylcarbamoyl]ethyl}-3-(4-chloro-2-fluorobenzenesulfonylamino)-2-methanesulfonylaminopropionamide. The desired product is obtained with MW=676.13 (calculated, monoisotopic); measured value (M+H)+: 677.14 c) 3-Amino-6-(4-chlorobenzyl)-1-(4-chloro-2-fluorobenzenesulfonyl)-8-isopropylhexahydropyrazino[1,2-a]pyrimidine-4,7-dione Synthesis takes place in analogy to Example 1g) (Method B) starting from benzyl [6-(4-chlorobenzyl)-1-(4-chloro-2-fluorobenzenesulfonyl)-8-isopropyl-4,7-dioxooctahydropyrazino[1,2-a]pyrimidin-3-yl]carbamate. The desired product is obtained with MW=542.1 (calculated, monoisotopic); measured value (M+H)+: 543.1 d) N-[6-(4-Chlorobenzyl)-1-(4-chloro-2-fluorobenzenesulfonyl)-8-isopropyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(4-chlorobenzyl)-1-(4-chloro-2-fluorobenzenesulfonyl)-8-isopropylhexahydropyrazino[1,2-a]pyrimidine-4,7-dione. The desired product is obtained with MW=738.22 (calculated, monoisotopic); measured value (M+H)+: 739.20

Example 9

N-[1-(2,4-Dichlorobenzenesulfonyl)-6-(3,4-difluorobenzyl)-8-isopropyl-4,7-dioxooctahydropyrazino[1,2-a]pyrimidin-3-yl]-1-(2-amino-3-methylbutyryl)pyrrolidine-2-carboxamide

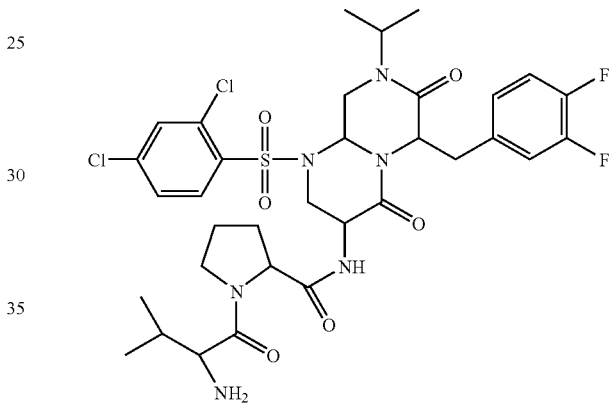

a) 9H-Fluoren-9-ylmethyl [1-[(2,2-diethoxyethyl)isopropylcarbamoyl]-2-(3,4-difluorophenyl)ethyl]carbamate Synthesis takes place in analogy to Example 1a) (Method B) starting from N-Fmoc-3,4-F2-Phe-OH. The desired product is obtained with MW=580.27 (calculated, monoisotopic); measured value (M+Na)+: 603.25.

b) 2-Amino-3-(3,4-difluorophenyl)-N-(2,2-diethoxyethyl)-N-isopropylpropionamide

Synthesis takes place in analogy to Example 1b) (Method B) starting from 9H-fluoren-9-ylmethyl [1-[(2,2-diethoxyethyl)isopropylcarbamoyl]-2-(3,4-difluorophenyl)ethyl]carbamate. The desired product is obtained with MW=358.21 (calculated, monoisotopic); measured value (M+H)+: 359.2.

c) 9H-Fluoren-9-ylmethyl (2-benzyloxycarbonylamino-2-{2-(3,4-difluorophenyl)-1-[(2,2-diethoxyethyl)isopropylcarbamoyl]ethylcarbamoyl}ethyl)carbamate Synthesis took place in analogy to Example 1c) (Method B) starting from 2-amino-3-(3,4-difluorophenyl)-N-(2,2-diethoxyethyl)-N-isopropylpropionamide. The desired product is obtained with MW=800.36 (calculated, monoisotopic); measured value (M+H)+: 801.35.

d) Benzyl (2-amino-1-{2-(3,4-difluorophenyl)-1-[(2,2-diethoxyethyl)isopropylcarbamoyl]-ethylcarbamoyl}ethyl)carbamate Synthesis took place in analogy to Example 1d) (Method B) starting from 9H-fluoren-9-ylmethyl (2-benzyloxycarbonylamino-2-{2-(3,4-difluorophenyl)-1-[(2,2-diethoxyethyl)isopropylcarbamoyl]ethylcarbamoyl}ethyl)carbamate. The desired product is obtained with MW=578.29 (calculated, monoisotopic); measured value (M+H)+: 579.31.

e) Benzyl [1-{2-(3,4-difluorophenyl)-1-[(2,2-diethoxyethyl)isopropylcarbamoyl]ethylcarbamoyl}-2-(2,4-dichlorobenzenesulfonylamino)ethyl]carbamate Synthesis took place in analogy to Example 1e) (Method B) starting from benzyl (2-amino-1-{2-(3,4-difluorophenyl)-1-[(2,2-diethoxyethyl)isopropylcarbamoyl]ethylcarbamoyl}ethyl)carbamate. The desired product is obtained with MW=786.21 (calculated, monoisotopic); measured value (M+Na)+: 809.19.

f) Benzyl [6-(3,4-difluorobenzyl)-1-(2,4-dichlorobenzenesulfonyl)-8-isopropyl-4,7-dioxooctahydropyrazino[1,2-a]pyrimidin-3-yl]carbamate Synthesis took place in analogy to Example 1f) (Method B) starting from benzyl [1-{2-(3,4-difluorophenyl)-1-[(2,2-diethoxyethyl)isopropylcarbamoyl]ethylcarbamoyl}-2-(2,4-dichlorobenzenesulfonylamino)ethyl]carbamate. The desired product is obtained with MW=694.12 (calculated, monoisotopic); measured value (M+H)+: 695.10.

g) 3-Amino-6-(3,4-difluorobenzyl)-1-(2,4-dichlorobenzenesulfonyl)-8-isopropylhexahydropyrazino[1,2-a]pyrimidine-4,7-dione Synthesis took place in analogy to Example 1g) (Method B) starting from benzyl [6-(3,4-difluorobenzyl)-1-(2,4-dichlorobenzenesulfonyl)-8-isopropyl-4,7-dioxooctahydropyrazino[1,2-a]pyrimidin-3-yl]carbamate. The desired product is obtained with MW=560.09 (calculated, monoisotopic); measured value (M+H)+: 561.13.

h) N-[1-(2,4-dichlorobenzenesulfonyl)-6-(3,4-difluorobenzyl)-8-isopropyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(3,4-difluorobenzyl)-1-(2,4-dichlorobenzenesulfonyl)-8-isopropylhexahydropyrazino[1,2-a]pyrimidine-4,7-dione. The desired product is obtained with MW=756.21 (calculated, monoisotopic); measured value (M+H)+: 757.21.

Example 10

N-[1-(2,4-Dichlorobenzenesulfonyl)-6-(2,4-difluorobenzyl)-8-isopropyl-4,7-dioxooctahydropyrazino[1,2-a]pyrimidin-3-yl]-1-(2-amino-3-methylbutyryl)pyrrolidine-2-carboxamide

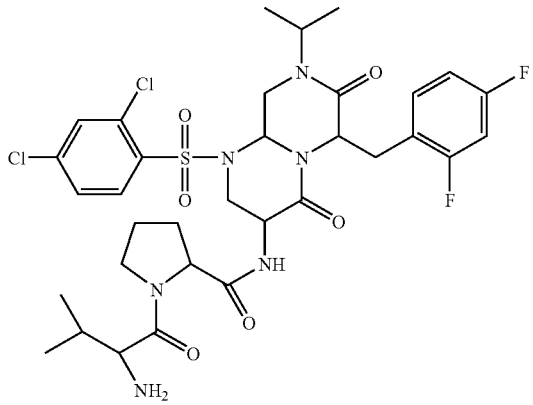

a) 2-Allyloxycarbonylamino-3-(2,4-difluorophenyl)propionic acid

Synthesis takes place in analogy to Example 1a) (Method A) starting from 2-amino-3-(2,4-difluorophenyl)propionic acid. The desired product is obtained with MW=285.08 (calculated, monoisotopic); measured value (M+H)+: 286.05.

b) Allyl {2-(2,4-difluorophenyl)-1-[(2,2-diethoxyethyl)isopropylcarbamoyl]ethyl}-carbamate Synthesis takes place in analogy to Example 1b) (Method A) starting from 2-allyloxycarbonylamino-3-(2,4-difluorophenyl)propionic acid. The desired product is obtained with MW=442.23 (calculated, monoisotopic); measured value (M+H)+: 443.2.

c) 2-Amino-3-(2,4-difluorophenyl)-N-(2,2-diethoxyethyl)-N-isopropylpropionamide

Synthesis takes place in analogy to Example 1c) (Method A) starting from allyl {2-(2,4-difluorophenyl)-1-[(2,2-diethoxyethyl)isopropylcarbamoyl]ethyl}carbamate. The desired product is obtained with MW=358.21 (calculated, monoisotopic); measured value (M+H)+: 359.2.

d) Benzyl (2-(2,4-dichlorobenzenesulfonylamino)-1-{2-(2,4-difluorophenyl)-1-[(2,2-diethoxyethyl)isopropylcarbamoyl]ethylcarbamoyl}ethyl)carbamate Synthesis takes place in analogy to Example 1d) (Method A) starting from 2-amino-3-(2,4-difluorophenyl)-N-(2,2-diethoxyethyl)-N-isopropylpropionamide. The desired product is obtained with MW=786.21 (calculated, monoisotopic); measured value (M+H)+: 787.30.

e) Benzyl [6-(2,4-difluorobenzyl)-1-(2,4-dichlorobenzenesulfonyl)-8-isopropyl-4,7-dioxooctahydropyrazino[1,2-a]pyrimidin-3-yl]carbamate Synthesis takes place in analogy to Example 1f) (Method A) starting from benzyl (2-(2,4-dichlorobenzenesulfonylamino)-1-{2-(2,4-difluorophenyl)-1-[(2,2-diethoxyethyl)isopropylcarbamoyl]ethylcarbamoyl}ethyl)carbamate. The desired product is obtained with MW=694.12 (calculated, monoisotopic); measured value (M+H)$^+$: 695.05.

f) 3-Amino-6-(2,4-difluorobenzyl)-1-(2,4-dichlorobenzenesulfonyl)-8-isopropylhexahydropyrazino[1,2-a]pyrimidine-4,7-dione Synthesis takes place in analogy to Example 1g) (Method A) starting from benzyl (2-(2,4-dichlorobenzenesulfonylamino)-1-{2-(2,4-difluorophenyl)-1-[(2,2-diethoxyethyl)isopropylcarbamoyl]ethylcarbamoyl}ethyl)carbamate. The desired product is obtained with MW=560.09 (calculated, monoisotopic); measured value (M+H)$^+$: 561.0.

g) N-[1-(2,4-Dichlorobenzenesulfonyl)-6-(2,4-difluorobenzyl)-8-isopropyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) (Method A) starting from 3-amino-6-(2,4-difluorobenzyl)-1-(2,4-dichlorobenzenesulfonyl)-8-isopropylhexahydropyrazino[1,2-a]pyrimidine-4,7-dione. The desired product is obtained with MW=756.21 (calculated, monoisotopic); measured value (M+H)$^+$: 757.20.

Example 11

N-[6-(4-Chlorobenzyl)-1-(2,4-dichlorobenzenesulfonyl)-8-(2,2-difluoroethyl)-4,7-dioxooctahydropyrazino[1,2-a]pyrimidin-3-yl]-1-(2-amino-3-methylbutyryl)pyrrolidine-2-carboxamide

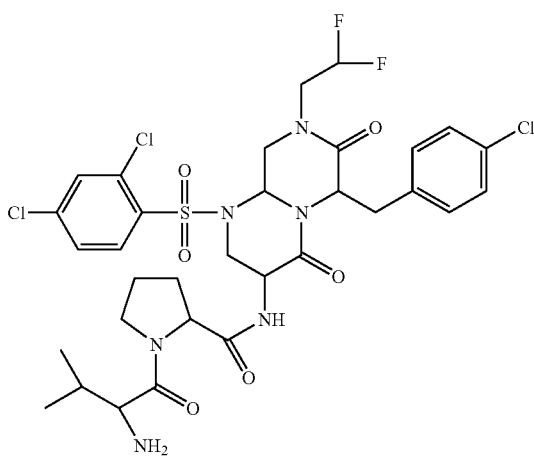

a) (2,2-Diethoxyethyl)-(2,2-difluoroethyl)amine

A solution of 3 g (22.5 mM) of 1-amino-2,2-diethoxyethane, 3.1 g (24.8 mM) of difluoroacetaldehyde ethyl hemiacetal and 1 pellet of solid NaOH in 44 ml of toluene was heated at 120° C. with a Dean-Stark trap for 1.5 hours. The mixture is left to stand until it has cooled to room temperature and is concentrated in vacuo. The residue is diluted with 80 ml of methanol, and 3.4 g (90 mM) of sodium borohydride were added in small quantities. The reaction mixture is then stirred overnight, concentrated in vacuo and partitioned between ethyl acetate and water. The organic phase is isolated, dried (MgSO$_4$) and concentrated in vacuo. 3.7 g of crude substance are obtained as a colorless oil. The residue is subjected to a flash chromatography on 40 g of SiO$_2$ (elution with DCM/MeOH, gradient 1-8%). 3.1 g of the desired amine were obtained as a colorless oil.

b) 2-Amino-3-(4-chlorophenyl)-N-(2,2-diethoxyethyl)-N-(2,2-difluoroethyl)propionamide A solution of 1.0 g (2.37 mm) of Fmoc-Phe(4-Cl)—OH and 489 mg (2.61 mm) of the amine (2,2-diethoxyethyl)-(2,2-difluoroethyl)-amine is dissolved in 9.5 ml of dimethylformamide. 722 mg (2.61 mm) of DMTMM are added to this solution. The mixture is stirred at room temperature overnight, diluted with ethyl acetate and washed with water and brine. The organic phase is isolated, dried (MgSO$_4$) and concentrated in vacuo. The residue is chromatographed on 40 g of SiO$_2$ (elution with EtOAc/heptane, gradient 10-70%). 890 mg of the substance are obtained as a white foam. LC/MS M$^+$=591, measured value (M$^+$Na)=613 and M−OEt=545 agreed with the desired substance. A solution of 890 mg (1.5 mm) of said substance is dissolved in 7.5 ml of dimethylformamide, and 0.8 ml of diethylamine is added. The reaction mixture is stirred at room temperature for 10 minutes and concentrated in vacuo. The residue is subjected to a flash chromatography on 12 g of SiO$_2$ (elution with MeOH in DCM, gradient 1-10%). The desired product is obtained with MW=378.15 (calculated, monoisotopic); measured value (M+H)$^+$: 379.18.

c) Benzyl [1-{2-(4-chlorophenyl)-1-[(2,2-diethoxyethyl)-(2,2-difluoroethyl)carbamoyl]-ethylcarbamoyl}-2-(2,4-dichlorobenzenesulfonylamino)ethyl]carbamate A solution of 2.5 g (10.5 mm) of Z-Dap-OH in 21 ml of 1N NaOH is stirred until homogeneous. A solution of 2.83 g (11.5 mm) of 2,4-dichlorophenylsulfonyl chloride in 29 ml of dioxane is slowly added to the Z-Dap-OH solution. The mixture is then stirred for 2 hours. The reaction mixture is acidified with citric acid and extracted with DCM. The organic phase is dried (MgSO$_4$) and concentrated in vacuo. 4.08 g of the desired sulfonamide are obtained and are employed without further purification in the process described below. 755 mg (2.7 mm) of DMTMM are added to a solution of 840 mg (2.2 mm) of 2-amino-3-(4-chlorophenyl)-N-(2,2-diethoxyethyl)-N-(2,2-difluoroethyl)propionamide and 1.22 g (2.7 mm) of said sulfonamide in 9 ml of DMF. The mixture is stirred at room temperature for 2 days, diluted with ethyl acetate and washed with water and brine. The organic phase is isolated, dried (MgSO$_4$) and concentrated in vacuo. 1.9 g of crude substance are obtained as a white foam. The residue is subjected to a flash chromatography on 40 g of SiO$_2$ (elution with EtOAc/heptane, gradient 10-80%). The desired product is obtained with MW=806.15 (calculated, monoisotopic); measured value (M+Na)$^+$: 829.11.

d) Benzyl [6-(4-chlorobenzyl)-1-(2,4-dichlorobenzenesulfonyl)-8-(2,2-difluoroethyl)-4,7-dioxooctahydropyrazino[1,2-a]pyrimidin-3-yl]carbamate Synthesis takes place in analogy to Example 1f) (Method B) starting from benzyl [1-{2-(4-chlorophenyl)-1-[(2,2-diethoxyethyl)-(2,2-difluoroethyl)carbamoyl]ethylcarbamoyl}-2-(2,4-dichlorobenzenesulfonylamino)ethyl]carbamate. The desired product is obtained with MW=714.07 (calculated, monoisotopic); measured value (M+H)+: 715.02.

e) 3-Amino-6-(4-chlorobenzyl)-1-(2,4-dichlorobenzenesulfonyl)-8-(2,2-difluoroethyl)hexahydropyrazino[1,2-a]pyrimidine-4,7-dione Synthesis takes place in analogy to Example 1g) (Method B) starting from benzyl [6-(4-chlorobenzyl)-1-(2,4-dichlorobenzenesulfonyl)-8-(2,2-difluoroethyl)-4,7-dioxooctahydropyrazino[1,2-a]pyrimidin-3-yl]carbamate. The desired product is obtained with MW=580.03 (calculated, monoisotopic); measured value (M+H)+: 580.99.

f) N-[6-(4-Chlorobenzyl)-1-(2,4-dichlorobenzenesulfonyl)-8-(2,2-difluoroethyl)-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(4-chlorobenzyl)-1-(2,4-dichlorobenzenesulfonyl)-8-(2,2-difluoroethyl)hexahydropyrazino[1,2-a]pyrimidine-4,7-dione. The desired product is obtained with MW=776.15 (calculated, monoisotopic); measured value (M+H)+: 777.16.

Example 12

N-[6-(4-Chlorobenzyl)-1-(2,4-dichlorobenzenesulfonyl)-8-ethyl-4,7-dioxooctahydropyrazino[1,2-a]pyrimidin-3-yl]-1-(2-amino-3-methylbutyryl)pyrrolidine-2-carboxamide

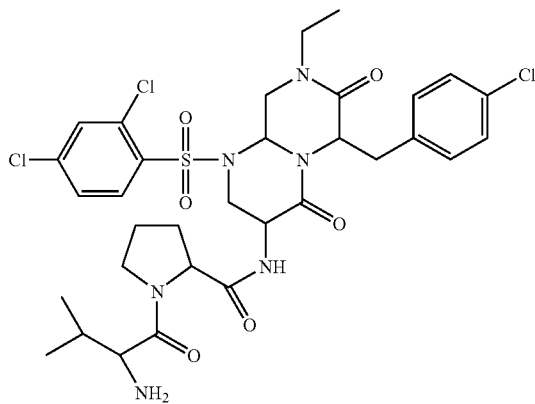

a) 9H-Fluoren-9-ylmethyl [1-[(2,2-diethoxyethyl)ethylcarbamoyl]-2-(4-chlorophenyl)ethyl]carbamate Synthesis takes place in analogy to Example 1a) (Method B) starting from N-Fmoc-4-Cl-Phe-OH and (2,2-diethoxyethyl)ethylamine. The desired product is obtained with MW 564.24=(calculated, monoisotopic); measured value (M+H)+: 565.3.

b) 2-Amino-3-(4-chlorophenyl)-N-(2,2-diethoxyethyl)-N-ethylpropionamide

Synthesis takes place in analogy to Example 1b) (Method B) starting from 9H-fluoren-9-ylmethyl [1-[(2,2-diethoxyethyl)ethylcarbamoyl]-2-(4-chlorophenyl)ethyl]carbamate. The desired product is obtained with MW=342.17 (calculated, monoisotopic); measured value (M+H)+: 343.12.

c) Benzyl [2-(9H-fluoren-9-ylmethoxycarbonylamino) [1-{2-(4-chlorophenyl)-1-[(2,2-diethoxyethyl)ethylcarbamoyl]ethylcarbamoyl}ethyl]carbamate Synthesis took place in analogy to Example 1c) (Method B) starting from 2-amino-3-(4-chlorophenyl)-N-(2,2-diethoxyethyl)-N-ethylpropionamide. The desired product is obtained with MW=784.32 (calculated, monoisotopic); measured value (M+H)+: 785.35.

d) Benzyl (2-amino-1-{2-(4-chlorophenyl)-1-[(2,2-diethoxyethyl)ethylcarbamoyl]-ethylcarbamoyl}ethyl)carbamate Synthesis took place in analogy to Example 1d) (Method B) starting from benzyl [2-(9H-fluoren-9-ylmethoxycarbonylamino)[1-{2-(4-chlorophenyl)-1-[(2,2-diethoxyethyl)ethyl]carbamoyl]ethylcarbamoyl}ethyl]carbamate. The desired product is obtained with MW=562.26 (calculated, monoisotopic); measured value (M+H)+: 563.2.

e) Benzyl [1-{2-(4-chlorophenyl)-1-[(2,2-diethoxyethyl)ethylcarbamoyl]ethylcarbamoyl}-2-(2,4-dichlorobenzenesulfonylamino)ethyl]carbamate Synthesis took place in analogy to Example 1e) (Method B) starting from benzyl (2-amino-1-{2-(4-chlorophenyl)-1-[(2,2-diethoxyethyl)ethylcarbamoyl]ethylcarbamoyl}ethyl)carbamate. The desired product is obtained with MW=770.17 (calculated, monoisotopic); measured value (M–CO$_2$+H)+: 727.13.

f) Benzyl [6-(4-chlorobenzyl)-1-(2,4-dichlorobenzenesulfonyl)-8-ethyl-4,7-dioxooctahydropyrazino[1,2-a]pyrimidin-3-yl]carbamate Synthesis took place in analogy to Example 1f) (Method B) starting from benzyl [1-{2-(4-chlorophenyl)-1-[(2,2-diethoxyethyl)ethylcarbamoyl]ethylcarbamoyl}-2-(2,4-dichlorobenzenesulfonylamino)ethyl]carbamate. The desired product is obtained with MW=678.09 (calculated, monoisotopic); measured value (M+H)+: 679.1.

g) 3-Amino-6-(4-chlorobenzyl)-1-(2,4-dichlorobenzenesulfonyl)-8-ethylhexa-hydropyrazino[1,2-a]pyrimidine-4,7-dione Synthesis takes place in analogy to Example 1g) (Method B) starting from benzyl [6-(4-chlorobenzyl)-1-(2,4-dichlorobenzenesulfonyl)-8-ethyl-4,7-dioxooctahydropyrazino[1,2-a]pyrimidin-3-yl]carbamate. The desired product is obtained with MW=544.05 (calculated, monoisotopic); measured value (M+H)+: 545.1.

h) N-[6-(4-Chlorobenzyl)-1-(2,4-dichlorobenzenesulfonyl)-8-ethyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(4-chlorobenzyl)-1-(2,4-dichlorobenzenesulfonyl)-8-ethylhexahydropyrazino[1,2-a]pyrimidine-4,7- dione. The desired product is obtained with MW=740.17 (calculated, monoisotopic); measured value (M+H)+: 741.19.

Example 13

N-[6-(4-Chlorobenzyl)-1-(2,4-dichlorobenzene-sulfonyl-8-methyl-4,7-dioxooctahydropyrazino[1,2-a]pyrimidin-3-yl]-1-(2-amino-3-methylbutyryl)pyrrolidine-2-carboxamide

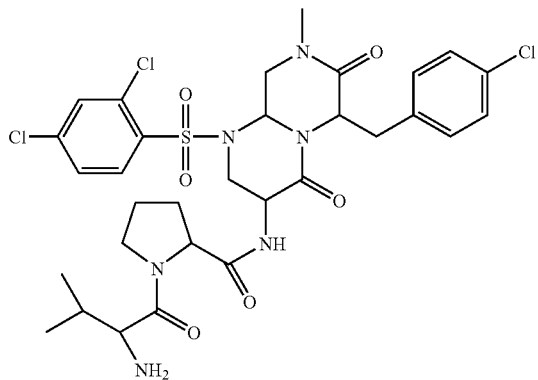

a) 9H-Fluoren-9-ylmethyl [1-[(2,2-diethoxyethyl)methylcarbamoyl]-2-(4-chlorophenyl)ethyl]carbamate Synthesis takes place in analogy to Example 1a) (Method B) starting from N-Fmoc-4-Cl-Phe-OH and (2,2-diethoxyethyl)methylamine. The desired product is obtained with MW=550.22 (calculated, monoisotopic); measured value (M+H)+: 551.2.

b) 2-Amino-3-(4-chlorophenyl)-N-(2,2-diethoxyethyl)-N-methylpropionamide

Synthesis takes place in analogy to Example 1b) (Method B) starting from 9H-fluoren-9-ylmethyl [1-[(2,2-diethoxyethyl)methylcarbamoyl]-2-(4-chlorophenyl)ethyl]carbamate. The desired product is obtained with MW=328.16 (calculated, monoisotopic); measured value (M+H)+: 329.2.

c) Benzyl [1-{2-(4-chlorophenyl)-1-[(2,2-diethoxyethyl)methylcarbamoyl]ethylcarbamoyl}-2-(9H-fluoren-9-ylmethoxycarbonylamino)ethyl]carbamate Synthesis took place in analogy to Example 1c) (Method B) starting from 2-amino-3-(4-chlorophenyl)-N-(2,2-diethoxyethyl)-N-methylpropionamide. The desired product is obtained with MW=770.31 (calculated, monoisotopic); measured value (M+H)+: 771.32.

d) Benzyl (2-amino-1-{2-(4-chlorophenyl)-1-[(2,2-diethoxyethyl)methylcarbamoyl]-ethylcarbamoyl}ethyl)carbamate Synthesis took place in analogy to Example 1d) (Method B) starting from benzyl [1-{2-(4-chlorophenyl)-1-[(2,2-diethoxyethyl)methylcarbamoyl]ethylcarbamoyl}-2-(9H-fluoren-9-ylmethoxycarbonylamino)ethyl]carbamate. The desired product is obtained with MW=548.24 (calculated, monoisotopic); measured value (M+H)+: 549.23.

e) Benzyl [1-{2-(4-chlorophenyl)-1-[(2,2-diethoxyethyl)methylcarbamoyl]ethylcarbamoyl}-2-(2,4-dichlorobenzenesulfonylamino)ethyl]carbamate Synthesis took place in analogy to Example 1e) (Method B) starting from benzyl (2-amino-1-{2-(4-chlorophenyl)-1-[(2,2-diethoxyethyl)methylcarbamoyl]ethylcarbamoyl}ethyl)carbamate. The desired product is obtained with MW=756.16 (calculated, monoisotopic); measured value (M+Na)+: 757.16.

f) Benzyl [6-(4-chlorobenzyl)-1-(2,4-dichlorobenzenesulfonyl)-8-methyl-4,7-dioxooctahydropyrazino[1,2-a]pyrimidin-3-yl]carbamate Synthesis took place in analogy to Example 1f) (Method B) starting from benzyl [1-{2-(4-chlorophenyl)-1-[(2,2-diethoxyethyl)methylcarbamoyl]ethylcarbamoyl}-2-(2,4-dichlorobenzenesulfonylamino)ethyl]carbamate. The desired product is obtained with MW=664.07 (calculated, monoisotopic); measured value (M+H)+: 665.07.

g) 3-Amino-6-(4-chlorobenzyl)-1-(2,4-dichlorobenzenesulfonyl)-8-methylhexa-hydropyrazino[1,2-a]pyrimidine-4,7-dione Synthesis takes place in analogy to Example 1g) (Method B) starting from benzyl [6-(4-chlorobenzyl)-1-(2,4-dichlorobenzenesulfonyl)-8-methyl-4,7-dioxooctahydropyrazino[1,2-a]pyrimidin-3-yl]carbamate. The desired product is obtained with MW=530.03 (calculated, monoisotopic); measured value (M+H)+: 531.1.

h) N-[6-(4-Chlorobenzyl)-1-(2,4-dichlorobenzenesulfonyl)-8-methyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(4-chlorobenzyl)-1-(2,4-dichlorobenzenesulfonyl)-8-methylhexahydropyrazino[1,2-a]pyrimidine-4,7-dione. The desired product is obtained with MW=726.16 (calculated, monoisotopic); measured value (M+H)+: 727.16.

Example 14

N-[1-(2,4-dichlorobenzenesulfonyl)-6-(3,4-difluorobenzyl)-8-ethyl-4,7-dioxooctahydropyrazino[1,2-a]pyrimidin-3-yl]-1-(2-amino-3-methylbutryl)pyrrolidine-2-carboxamide

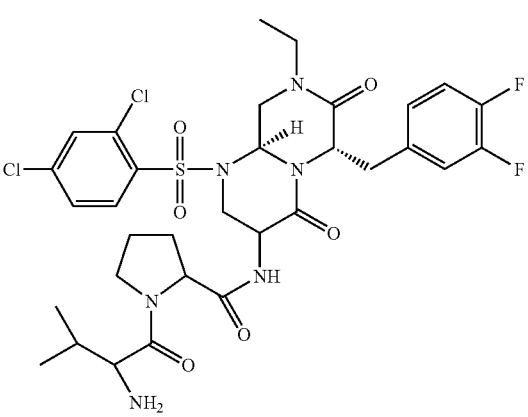

a) 9H-Fluoren-9-ylmethyl [1-[(2,2-diethoxyethyl)ethylcarbamoyl]-2-(3,4-difluorophenyl)ethyl]carbamate Synthesis takes place in analogy to Example 1a) (Method B) starting from N-Fmoc-3,4-diF-Phe-OH and (2,2-diethoxyethyl)ethylamine. The desired product is obtained with MW=566.26 (calculated, monoisotopic); measured value (M+H)+: 567.27.

b) 2-Amino-3-(3,4-difluorophenyl)-N-(2,2-diethoxyethyl)-N-ethylpropionamide

Synthesis takes place in analogy to Example 1b) (Method B) starting from 9H-fluoren-9-ylmethyl [1-[(2,2-diethoxyethyl)ethylcarbamoyl]-2-(3,4-difluorophenyl)ethyl]carbamate. The desired product is obtained with MW=344.19 (calculated, monoisotopic); measured value (M+H)+: 345.19.

c) Benzyl [1-{2-(3,4-difluorophenyl)-1-[(2,2-diethoxyethyl)ethylcarbamoyl]ethylcarbamoyl}-2-(9H-fluoren-9-ylmethoxycarbonylamino)ethyl]carbamate Synthesis took place in analogy to Example 1c) (Method B) starting from 2-amino-3-(3,4-difluorophenyl)-N-(2,2-diethoxyethyl)-N-ethylpropionamide. The desired product is obtained with MW=786.34 (calculated, monoisotopic); measured value (M+H)+: 787.4.

d) Benzyl (2-amino-1-{2-(3,4-difluorophenyl)-1-[(2,2-diethoxyethyl)ethylcarbamoyl]-ethylcarbamoyl}ethyl)carbamate Synthesis took place in analogy to Example 1d) (Method B) starting from benzyl [1-{2-(3,4-difluorophenyl)-1-[(2,2-diethoxyethyl)ethylcarbamoyl]ethylcarbamoyl}-2-(9H-fluoren-9-ylmethoxycarbonylamino)ethyl]carbamate. The desired product is obtained with MW=564.28 (calculated, monoisotopic); measured value (M+H)+: 565.27.

e) Benzyl [1-{2-(3,4-difluorophenyl)-1-[(2,2-diethoxyethyl)ethylcarbamoyl]ethylcarbamoyl}-2-(2,4-dichlorobenzenesulfonylamino)ethyl]carbamate Synthesis took place in analogy to Example 1e) (Method B) starting from benzyl (2-amino-1-{2-(3,4-difluorophenyl)-1-[(2,2-diethoxyethyl)ethylcarbamoyl]ethylcarbamoyl}ethyl)carbamate. The desired product is obtained with MW=772.19 (calculated, monoisotopic); measured value (M+H)+: 773.3.

f) Benzyl [6-(3,4-difluorobenzyl)-1-(2,4-dichlorobenzenesulfonyl)-8-ethyl-4,7-dioxooctahydropyrazino[1,2-a]pyrimidin-3-yl]carbamate Synthesis took place in analogy to Example 1f) (Method B) starting from benzyl [1-{2-(3,4-difluorophenyl)-1-[(2,2-diethoxyethyl)ethylcarbamoyl]ethylcarbamoyl}-2-(2,4-dichlorobenzenesulfonylamino)ethyl]carbamate. The desired product is obtained with MW=680.17 (calculated, monoisotopic); measured value (M+H)+: 681.1.

g) 3-Amino-6-(3,4-difluorobenzyl)-1-(2,4-dichlorobenzenesulfonyl)-8-ethylhexahydropyrazino[1,2-a]pyrimidine-4,7-dione Synthesis takes place in analogy to Example 1g) (Method B) starting from benzyl [6-(3,4-difluorobenzyl)-1-(2,4-dichlorobenzenesulfonyl)-8-ethyl-4,7-dioxooctahydropyrazino[1,2-a]pyrimidin-3-yl]carbamate. The desired product is obtained with MW=546.07 (calculated, monoisotopic); measured value (M+H)+: 547.1.

h) N-[6-(3,4-Difluorobenzyl)-1-(2,4-dichlorobenzenesulfonyl)-8-ethyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(3,4-difluorobenzyl)-1-(2,4-dichlorobenzenesulfonyl)-8-ethylhexahydropyrazino[1,2-a]pyrimidine-4,7-dione. The desired product is obtained with MW=742.19 (calculated, monoisotopic); measured value (M+H)+: 743.21.

Example 15

N-[1-(2,4-Dichlorobenzenesulfonyl)-6-(3,4-difluorobenzyl)-8-methyl-4,7-dioxooctahydropyrazino[1,2-a]pyrimidin-3-yl]-1-(2-amino-3-methylbutyryl)pyrrolidine-2-carboxamide

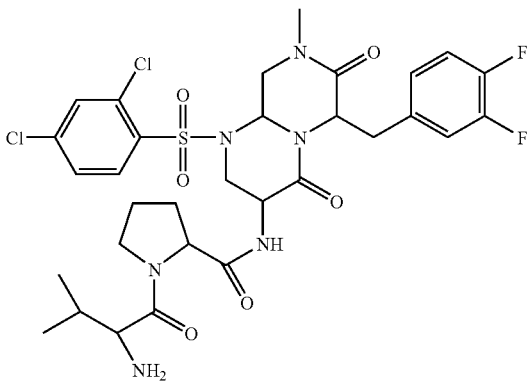

a) 9H-Fluoren-9-ylmethyl [1-[(2,2-diethoxyethyl)methylcarbamoyl]-2-(3,4-difluorophenyl)ethyl]carbamate Synthesis takes place in analogy to Example 1a) (Method B) starting from N-Fmoc-3,4-diF-Phe-OH and (2,2-diethoxyethyl)methylamine. The desired product is obtained with MW=552.24 (calculated, monoisotopic); measured value (M+H)+: 553.25.

b) 2-Amino-3-(3,4-difluorophenyl)-N-(2,2-diethoxyethyl)-N-methylpropionamide Synthesis takes place in analogy to Example 1b) (Method B) starting from 9H-fluoren-9-ylmethyl [1-[(2,2-diethoxyethyl)methylcarbamoyl]-2-(3,4-difluorophenyl)ethyl]carbamate. The desired product is obtained with MW=330.18 (calculated, monoisotopic); measured value (M+H)+: 331.18.

c) Benzyl [1-{2-(3,4-difluorophenyl)-1-[(2,2-diethoxyethyl)methylcarbamoyl]ethylcarbamoyl}-2-(9H-fluoren-9-ylmethoxycarbonylamino)ethyl]carbamate Synthesis takes place in analogy to Example 1c) (Method B) starting from 2-amino-3-(3,4-difluorophenyl)-N-(2,2-diethoxyethyl)-N-methylpropionamide. The desired product is obtained with MW=772.32 (calculated, monoisotopic); measured value (M+H)$^+$: 773.3.

d) Benzyl (2-amino-1-{2-(3,4-difluorophenyl)-1-[(2,2-diethoxyethyl)methylcarbamoyl]-ethylcarbamoyl}ethyl)carbamate Synthesis takes place in analogy to Example 1d) (Method B) starting from benzyl [1-{2-(3,4-difluorophenyl)-1-[(2,2-diethoxyethyl)methylcarbamoyl]ethylcarbamoyl}-2-(9H-fluoren-9-ylmethoxycarbonylamino)ethyl]carbamate. The desired product is obtained with MW=550.26 (calculated, monoisotopic); measured value (M+H)$^+$: 551.24.

e) Benzyl [1-{2-(3,4-difluorophenyl)-1-[(2,2-diethoxyethyl)methylcarbamoyl]ethylcarbamoyl}-2-(2,4-dichlorobenzenesulfonylamino)ethyl]carbamate Synthesis takes place in analogy to Example 1e) (Method B) starting from benzyl (2-amino-1-{2-(3,4-difluorophenyl)-1-[(2,2-diethoxyethyl)methylcarbamoyl]ethylcarbamoyl}ethyl)carbamate. The desired product is obtained with MW=758.18 (calculated, monoisotopic); measured value (M+H)$^+$: 759.3.

f) Benzyl [6-(3,4-difluorobenzyl)-1-(2,4-dichlorobenzenesulfonyl)-8-methyl-4,7-dioxooctahydropyrazino[1,2-a]pyrimidin-3-yl]carbamate Synthesis takes place in analogy to Example 1f) (Method B) starting from benzyl [1-{2-(3,4-difluorophenyl)-1-[(2,2-diethoxyethyl)methylcarbamoyl]methylcarbamoyl}-2-(2,4-dichlorobenzenesulfonylamino)ethyl]carbamate. The desired product is obtained with MW=666.09 (calculated, monoisotopic); measured value (M+H)$^+$: 667.1.

g) 3-Amino-6-(3,4-difluorobenzyl)-1-(2,4-dichlorobenzenesulfonyl)-8-methylhexahydropyrazino[1,2-a]pyrimidine-4,7-dione Synthesis takes place in analogy to Example 1g) (Method B) starting from benzyl [6-(3,4-difluorobenzyl)-1-(2,4-dichlorobenzenesulfonyl)-8-methyl-4,7-dioxooctahydropyrazino[1,2-a]pyrimidin-3-yl]carbamate. The desired product is obtained with MW=532.06 (calculated, monoisotopic); measured value (M+H)$^+$: 533.1.

h) N-[6-(3,4-Difluorobenzyl)-1-(2,4-dichlorobenzenesulfonyl)-8-methyl-4,7-dioxooctahydropyrazino[1,2-a]pyrimidin-3-yl]-1-(2-amino-3-methylbutyryl)pyrrolidine-2-carboxamide Synthesis takes place in analogy to Example 1h) starting from 3-amino-6-(3,4-difluorobenzyl)-1-(2,4-dichlorobenzenesulfonyl)-8-methyl hexahydropyrazino[1,2-a]pyrimidine-4,7-dione. The desired product is obtained with MW=728.18 (calculated, monoisotopic); measured value (M+H)$^+$: 729.18.

Example 16

N-[1-(2,4-Dichlorobenzenesulfonyl)-8-isopropyl-4,7-dioxo-6-pyridin-3-ylmethyloctahydropyrazino[1,2-a]pyrimidin-3-yl]-1-(2-amino-3-methylbutyryl)pyrrolidine-2-carboxamide

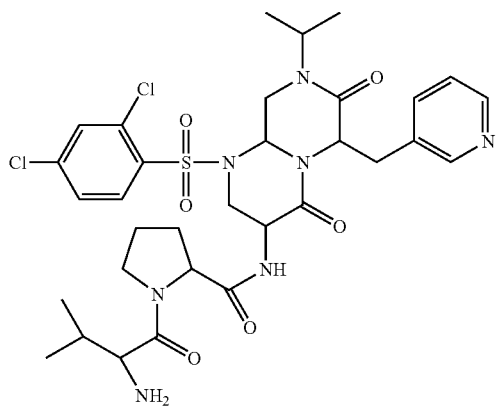

a) 9H-Fluoren-9-ylmethyl {1-[(2,2-diethoxyethyl)isopropylcarbamoyl]-2-pyridin-3-ylethyl}carbamate Synthesis takes place in analogy to Example 1a) (Method B) starting from Fmoc-3-pyridylalanine. The desired product is obtained with MW=545.29 (calculated, monoisotopic); measured value (M+H)$^+$: 546.24.

b) 2-Amino-N-(2,2-diethoxyethyl)-N-isopropyl-3-pyridin-3-ylpropionamide

Synthesis takes place in analogy to Example 1b) (Method B) starting from 9H-fluoren-9-ylmethyl {1-[(2,2-diethoxyethyl)isopropylcarbamoyl]-2-pyridin-3-ylethyl}carbamate. The desired product is obtained with MW=323.22 (calculated, monoisotopic); measured value (M+H)$^+$: 324.22.

c) Benzyl [1-[(2,2-diethoxyethyl)isopropylcarbamoyl]-2-pyridin-1-ylethylcarbamoyl}-2-(9H-fluoren-9-ylmethoxycarbonylamino)ethyl]carbamate Synthesis takes place in analogy to Example 1c) (Method B) starting from 2-amino-N-(2,2-diethoxyethyl)-N-isopropyl-3-pyridin-3-ylpropionamide. The desired product is obtained with MW=765.37 (calculated, monoisotopic); measured value (M+H)$^+$: 766.31.

d) Benzyl (2-amino-{1-[(2,2-diethoxyethyl)isopropylcarbamoyl]-2-pyridin-3-ylethylcarbamoyl}ethyl) carbamate Synthesis takes place in analogy to Example 1d) (Method B) starting from benzyl [1-[(2,2-diethoxyethyl)isopropylcarbamoyl]-2-pyridin-3-ylethylcarbamoyl}-2-(9H-fluoren-9-ylmethoxycarbonylamino)ethyl]carbamate. The desired product is obtained with MW=543.31 (calculated, monoisotopic); measured value (M+H)$^+$: 544.4.

e) Benzyl (2-(2,4-dichlorobenzenesulfonylamino)-1-{1-[(2,2-diethoxyethyl)isopropylcarbamoyl]-2-pyridin-3-ylethylcarbamoyl}ethyl)carbamate Synthesis takes place in analogy to Example 1e) (Method B) starting from benzyl (2-amino-{1-[(2,2-diethoxyethyl)isopropylcarbamoyl]-2-pyridin-3-ylethylcarbamoyl}ethyl)carbamate. The desired product is obtained with MW=751.22 (calculated, monoisotopic); measured value (M+H)$^+$: 752.19.

f) Benzyl [1-(2,4-dichlorobenzenesulfonyl)-8-isopropyl-4,7-dioxo-6-pyridin-1-ylmethyloctahydropyrazino[1,2-a]pyrimidin-3-yl]carbamate Synthesis takes place in analogy to Example 1f) starting from benzyl (2-(2,4-dichlorobenzenesulfonylamino)-1-{1-[(2,2-diethoxyethyl)isopropylcarbamoyl]-2-pyridin-3-ylethylcarbamoyl}ethyl)carbamate. The desired product is obtained with MW=659.14 (calculated, monoisotopic); measured value (M+H)$^+$: 660.10.

g) 3-Amino-1-(2,4-dichlorobenzenesulfonyl)-8-isopropyl-6-pyridin-3-ylmethylhexahydropyrazino[1,2-a]pyrimidine-4,7-dione Synthesis takes place in analogy to Example 1g) starting from benzyl [1-(2,4-dichlorobenzenesulfonyl)-8-isopropyl-4,7-dioxo-6-pyridin-1-ylmethyloctahydropyrazino[1,2-a]pyrimidin-3-yl]carbamate. The desired product is obtained with MW=525.10 (calculated, monoisotopic); measured value (M+H)$^+$: 526.1.

h) N-[1-(2,4-Dichlorobenzenesulfonyl)-8-isopropyl-4,7-dioxo-6-pyridin-3-ylmethyloctahydropyrazino[1,2-a]pyrimidin-3-yl]-1-(2-amino-3-methylbutyryl)pyrrolidine-2-carboxamide Synthesis takes place in analogy to Example 1h) starting from 3-amino-1-(2,4-dichlorobenzenesulfonyl)-8-isopropyl-6-pyridin-3-ylmethylhexahydropyrazino[1,2-a]pyrimidine-4,7-dione. The desired product is obtained with MW=721.22 (calculated, monoisotopic); measured value (M+H)$^+$: 722.23.

Example 17

N-[8-Cyclopropyl-1-(2,4-dichlorobenzenesulfonyl)-4,7-dioxo-6-pyridin-3-ylmethyloctahydropyrazino[1,2-a]pyrimidin-3-yl]-1-(2-amino-3-methylbutyryl)pyrrolidine-2-carboxamide

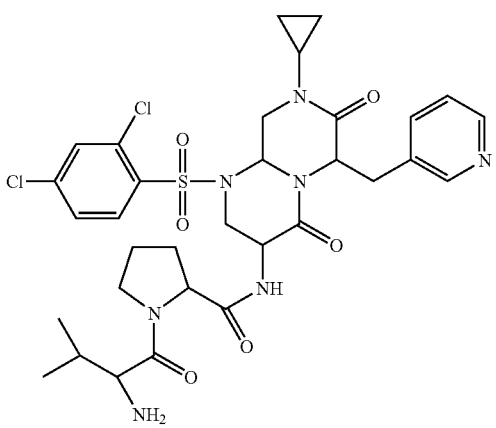

a) 9H-Fluoren-9-ylmethyl {1-[cyclopropyl(2,2-diethoxyethyl)carbamoyl]-2-pyridin-3-ylethyl}carbamate Synthesis takes place in analogy to Example 1a) (Method B) starting from Fmoc-PAL-OH and cyclopropyl(2,2-diethoxyethyl)amine. The desired product is obtained with MW=543.27 (calculated, monoisotopic); measured value (M+H)$^+$: 544.21.

b) 2-Amino-N-cyclopropyl-N-(2,2-diethoxyethyl)-2-pyridin-1-ylpropionamide

Synthesis takes place in analogy to Example 1b) (Method B) starting from 9H-fluoren-9-ylmethyl {1-[cyclopropyl(2,2-diethoxyethyl)carbamoyl]-2-pyridin-3-yl-ethyl}carbamate. The desired product is obtained with MW=321.21 (calculated, monoisotopic); measured value (M+H)$^+$: 322.20.

c) Benzyl [1-{1-[cyclopropyl(2,2-diethoxyethyl)carbamoyl]-2-pyridin-3-ylethylcarbamoyl}-2-(9H-fluoren-9-ylmethoxycarbonylamino)ethyl]carbamate Synthesis takes place in analogy to Example 1c) (Method B) starting from 2-amino-N-cyclopropyl-N-(2,2-diethoxyethyl)-3-pyridin-3-ylpropionamide. The desired product is obtained with MW=798.34 (calculated, monoisotopic); measured value (M+Na)$^+$: 821.35.

d) Benzyl (2-amino-1-{1-[cyclopropyl(2,2-diethoxyethyl)carbamoyl]-2-pyridin-3-ylethylcarbamoyl}ethyl)carbamate Synthesis took place in analogy to Example 1d) (Method B) starting from benzyl [1-{1-[cyclopropyl(2,2-diethoxyethyl)carbamoyl]-2-pyridin-3-ylethylcarbamoyl}-2-(9H-fluoren-9-ylmethoxycarbonylamino)ethyl]carbamate. The desired product is obtained with MW=541.29 (calculated, monoisotopic); measured value (M+H)$^+$: 542.30.

e) Benzyl [1-{1-[cyclopropyl (2,2-diethoxyethyl)carbamoyl]-2-pyridin-3-ylethylcarbamoyl}-2-(2,4-dichlorobenzenesulfonylamino)ethyl]carbamate Synthesis takes place in analogy to Example 1e) (Method B) starting from benzyl (2-amino-1-{1-[cyclopropyl(2,2-diethoxyethyl)carbamoyl]-2-pyridin-3-ylethylcarbamoyl}-ethyl)carbamate. The desired product is obtained with MW=826.12 (calculated, monoisotopic); measured value (M+Na)$^+$: 849.14.

f) Benzyl [8-cyclopropyl-1-(2,4-dichlorobenzenesulfonyl)-4,7-dioxo-6-pyridin-3-ylmethyloctahydropyrazino[1,2-a]pyrimidin-3-yl]carbamate Synthesis takes place in analogy to Example 1f) (Method B) starting from benzyl [1-{1-[cyclopropyl(2,2-diethoxyethyl)carbamoyl]-2-pyridin-3-ylethylcarbamoyl}-2-(2,4-dichlorobenzenesulfonylamino)ethyl]carbamate. The desired product is obtained with MW=657.12 (calculated, monoisotopic); measured value (M+H)$^+$: 658.11.

45 g) 3-Amino-8-cyclopropyl-1-(2,4-dichlorobenzene-sulfonyl)-6-pyridin-3-ylmethylhexahydropyrazino[1,2-a]pyrimidine-4,7-dione Synthesis takes place in analogy to Example 1g) (Method B) starting from benzyl [8-cyclopropyl-1-(2,4-dichlorobenzenesulfonyl)-4,7-dioxo-6-pyridin-3-ylmethyloctahydropyrazino[1,2-a]pyrimidin-3-yl]carbamate. The desired product is obtained with MW=523.08 (calculated, monoisotopic); measured value (M+H)$^+$: 524.09.

h) N-[8-Cyclopropyl-1-(2,4-dichlorobenzenesulfonyl)-4,7-dioxo-6-pyridin-3-ylmethyloctahydropyrazino[1,2-a]pyrimidin-3-yl]-1-(2-amino-3-methylbutyryl)pyrrolidine-2-carboxamide Synthesis takes place in analogy to Example 1h) starting from 3-amino-8-cyclopropyl-1-(2,4-dichlorobenzenesulfonyl)-6-pyridin-3-ylmethylhexahydropyrazino[1,2-a]pyrimidine-4,7-dione. The desired product is obtained with MW=719.21 (calculated, monoisotopic); measured value (M+H)$^+$: 720.21.

The invention claimed is:

1. A compound of formula I:

I wherein:
A is aryl or pyridyl, wherein said aryl or pyridyl may have one or more substituents selected from the group consisting of F, Cl, Br, NO$_2$, CF$_3$, OCF$_3$, CN, (C$_1$-C$_6$)-alkyl, aryl, CON(R11)(R12), N(R13)(R14), OH, O—(C$_1$-C$_6$)-alkyl, S—(C$_1$-C$_6$)-alkyl, N(R15)CO(C$_1$-C$_6$)-alkyl and COO—(C$_1$-C$_6$)-alkyl;
R11, R12, R13, R14, and R15 are, independently selected from the group consisting of, H, (C$_1$-C$_6$)-alkyl, or a heterocycle radical;
n is 0 or 1;
m is 1;
R1 is selected from the group consisting of R8, (C$_1$-C$_6$)-alkyl, (C$_1$-C$_6$)-alkylene-R8, (C$_2$-C$_6$)-alkenylene-R9, (SO$_2$)—R8, (SO$_2$)—(C$_1$-C$_6$)-alkylene-R8, (SO$_2$)—(C$_2$-C$_6$)-alkenylene-R9, (C═O)—R8, (C═O)—(C$_1$-C$_6$)-alkylene-R8, (C═O)NH—R8, (C═O)—(C$_2$-C$_6$)-alkenylene-R9, (C═O)—NH—(C$_1$-C$_6$)-alkylene-R8, (C═O)—NH—(C$_2$-C$_6$)-alkenylene-R9, COO—R8, COO—(C$_1$-C$_6$)-alkylene-R8, COO—(C$_2$-C$_6$)-alk-

46 enylene-R9, alkynylene-R9, and (C$_1$-C$_4$-alkyl)-heterocycle radical, wherein the alkylene may be substituted one or more times with F;
R8 and R9 are, independently of one another, H, F, Cl, Br, I, OH, CF$_3$, aryl, heterocycle radical, and (C$_3$-C$_8$)-cycloalkyl, wherein the rings or ring systems may be substituted up to 3 times with a substituent selected from F, Cl, Br, I, OH, CF$_3$, NO$_2$, CN, OCF$_3$, O—(C$_1$-C$_6$)-alkyl, (C$_1$-C$_6$)-alkyl, NH$_2$, CON(R11)(R12), N(R13)(R14), SO$_2$—CH$_3$, COOH, COO—(C$_1$-C$_6$)-alkyl, and CONH$_2$;
B is —NH(C═O)—;
R2 is a ring nitrogen-containing heterocyclyl, which is substituted with an amino acid via the carbonyl-terminus of the amino acid to the ring nitrogen atom of the heterocyclyl
R3 is H;
R4 and R5 are, independently of one another, H, F, Cl, Br, OH, CF$_3$, OCF$_3$, O—(C$_1$-C$_6$)-alkyl, or (C$_1$-C$_6$)-alkyl; and
R6 is H;
or a pharmaceutically acceptable salt thereof.

2. A compound of formula I,

Ia wherein:
A is phenyl or pyridyl, wherein said phenyl or pyridyl may have one or more further substituents selected from the group consisting of F, Cl, Br, NO$_2$, CF$_3$, OCF$_3$, CN, (C$_1$-C$_6$)-alkyl, and aryl;
m is 1;
n is 1;
R1 is (C$_1$-C$_6$)-alkyl, or (C$_3$-C$_8$)-cycloalkyl, wherein the alkyl may be substituted one or more times with F;
R1 is (C$_1$-C$_6$)-alkyl, or (C$_3$-C$_8$)-cycloalkyl, wherein the alkyl may be substituted one or more times with F;
B is —NH(C═O)—;
R2 is pyrrolidinyl which is substituted with an amino acid via the carbonyl-terminus of the amino acid to the ring nitrogen atom of the pyrrolidinyl
R3 is H;
R4 is F, Cl, Br, OH, CF$_3$, OCF$_3$, O—(C$_1$-C$_6$)-alkyl, or (C$_1$-C$_6$)-alkyl;
R5 is F, Cl, Br, OH, CF$_3$, OCF$_3$, O—(C$_1$-C$_6$)-alkyl, or (C$_1$-C$_6$)-alkyl; and
R6 is H;
or a pharmaceutically acceptable salt thereof.

* * * * *